(12) United States Patent
Fairweather

(10) Patent No.: US 7,308,674 B2
(45) Date of Patent: Dec. 11, 2007

(54) DATA FLOW SCHEDULING ENVIRONMENT WITH FORMALIZED PIN-BASE INTERFACE AND INPUT PIN TRIGGERING BY DATA COLLECTIONS

(76) Inventor: John Fairweather, 1649 Wellesley Dr., Santa Monica, CA (US) 90405

( * ) Notice: Subject to any disclaimer, the term of this patent is extended or adjusted under 35 U.S.C. 154(b) by 569 days.

(21) Appl. No.: 10/357,285

(22) Filed: Feb. 3, 2003

(65) Prior Publication Data

US 2003/0222912 A1    Dec. 4, 2003

Related U.S. Application Data

(60) Provisional application No. 60/353,487, filed on Feb. 1, 2002.

(51) Int. Cl.
*G06F 9/44* (2006.01)
(52) U.S. Cl. .................... 717/103; 717/132
(58) Field of Classification Search ............. 717/100, 717/108, 113, 125, 132, 103; 716/1, 18, 716/2
See application file for complete search history.

(56) References Cited

U.S. PATENT DOCUMENTS

| | | | | |
|---|---|---|---|---|
| 5,222,030 | A * | 6/1993 | Dangelo et al. | 716/11 |
| 5,526,277 | A * | 6/1996 | Dangelo et al. | 716/3 |
| 5,541,849 | A * | 7/1996 | Rostoker et al. | 716/18 |
| 5,544,066 | A * | 8/1996 | Rostoker et al. | 716/18 |
| 5,544,067 | A * | 8/1996 | Rostoker et al. | 703/14 |
| 5,553,002 | A * | 9/1996 | Dangelo et al. | 716/11 |
| 5,555,201 | A * | 9/1996 | Dangelo et al. | 716/1 |
| 5,557,531 | A * | 9/1996 | Rostoker et al. | 716/1 |
| 5,572,436 | A * | 11/1996 | Dangelo et al. | 716/18 |
| 5,572,437 | A * | 11/1996 | Rostoker et al. | 716/18 |
| 5,598,344 | A * | 1/1997 | Dangelo et al. | 716/18 |

(Continued)

OTHER PUBLICATIONS

ControlShell version 6.0 1999 by Real-Time Innovations Inc., User's Manual published Jan. 1999, Whole Manual.*

(Continued)

*Primary Examiner*—Todd Ingberg
(74) *Attorney, Agent, or Firm*—Merchant & Gould P.C.; Stanley J. Gradisar

(57) ABSTRACT

A system and method for implementing a data-flow based system includes three basic components: a data-flow based scheduling environment that balances the needs of data initiated program execution as a result of flows with other practical considerations such as user responsiveness, event driven invocation, user interface considerations, and the need to also support control-flow based paradigms where required; a visual programming language, based on the flow of strongly-typed run-time accessible data and data collections between small control-flow based locally and network distributed functional building-blocks, known as widgets; and a formalized pin-based interface to allow access to data-flow contents from the executing code within the widgets. The pins on the widgets include both pins used to control execution of a widget as well as pins used to receive data input from a data flow. The system and method further include a debugging environment that enables visual debugging of one or more widgets (or collections of widgets). Data control techniques include the concepts of "OR" and "AND" consumption thereby permitting either consumption immediately or only after all widget inputs have received the token. Additional extensions to this framework will also be described that relate to the environment, the programming language and the interface.

28 Claims, 11 Drawing Sheets

U.S. PATENT DOCUMENTS

| | | | |
|---|---|---|---|
| 5,623,418 A * | 4/1997 | Rostoker et al. | 716/1 |
| 5,801,958 A * | 9/1998 | Dangelo et al. | 716/18 |
| 5,867,399 A * | 2/1999 | Rostoker et al. | 716/18 |
| 5,870,308 A * | 2/1999 | Dangelo et al. | 716/18 |
| 5,910,897 A * | 6/1999 | Dangelo et al. | 716/19 |
| 6,075,935 A * | 6/2000 | Ussery et al. | 716/17 |
| 6,216,252 B1 * | 4/2001 | Dangelo et al. | 716/1 |
| 6,324,678 B1 * | 11/2001 | Dangelo et al. | 716/18 |
| 6,408,428 B1 * | 6/2002 | Schlansker et al. | 716/17 |
| 6,421,808 B1 * | 7/2002 | McGeer et al. | 716/1 |
| 6,484,304 B1 * | 11/2002 | Ussery et al. | 716/18 |
| 6,952,817 B1 * | 10/2005 | Harris et al. | 716/18 |
| 6,970,828 B2 * | 11/2005 | Castellani et al. | 705/8 |

OTHER PUBLICATIONS

"Beginning Visual C++5", Ivor Horton, Mar. 1997, pp. 798-803.*

* cited by examiner

DATA FLOW SCHEDULING ENVIRONMENT WITH FORMALIZED PIN-BASE INTERFACE AND INPUT PIN TRIGGERING BY DATA COLLECTIONS

CROSS REFERENCE TO RELATED APPLICATION

This application claims the benefit of U.S. Provisional Application Ser. No. 60/353,487 filed on Feb. 1, 2002 and titled "INTEGRATED MULTIMEDIA INTELLIGENCE ARCHITECTURE" which is incorporated herein by reference in its entirety for all that is taught and disclosed therein.

ENCORPORATION-BY-REFERENCE OF MATERIAL SUBMITTED ON A COMPACT DISC

Computer Program Listing—A computer program listing appendix is submitted on two compact discs (Copy 1 and Copy 2). These discs are identical to each other. Each disc includes four ASCII files comprising two computer program listing appendices and two reference appendices. All material therein is hereby incorporated by reference in its entirety in this application. The names and indicated sizes of the files on the compact discs are: Appendix A (8.8 Kbytes), a program listing for SC-Schedule View, SC-Schedule Node; SC-Schedule A Node, and SC-Start Widget; Appendix B (4.3 Kbytes), a program listing for Widget Pin Access API; Appendix 1 (28.8 Kbytes), a patent application titled "System and Method for Managing Memory" (the "Memory Patent Application"); and Appendix 2 (58.8 Kbytes), a patent application titled "A System for Exchanging Binary Data" (the "Types Patent Application"). These files include example source code illustrating specific implementations of specific embodiments of the invention along with explanatory text. These compact discs were created on Oct. 19, 2006 and are in IBM PC format and MS-Windows® operating system compatible.

BACKGROUND OF THE INVENTION

For complex systems, such as those designed for multimedia intelligence and knowledge management applications, the current 'control flow' based design methods are totally unsuitable. Once a system is broadened to include acquisition of unstructured, non-tagged, time-variant, multimedia information (much of which is designed specifically to prevent easy capture and normalization by non-recipient systems), a totally different approach is required. In this arena, many entrenched notions of information science and database methodology must be discarded to permit the problem to be addressed. We shall call systems that attempt to address this level of problem, 'Unconstrained Systems' (UCS). An unconstrained system is one in which the source(s) of data have no explicit or implicit knowledge of, or interest in, facilitating the capture and subsequent processing of that data by the system. The most significant challenges that must be resolved with the UCS is based on the following realities:

a) Change is the norm. The incoming data formats and content will change. The needs and requirements of the users of the data will also change. This will be reflected not only in their demands of the UI to the system, but also in the data model and field set that is to be captured and stored by the system.

b) An unconstrained system usually only samples from the flow going through the information pipe. The UCS is neither the source nor the destination for that flow, but simply a monitoring station attached to the pipe capable of selectively extracting data from the pipe as it passes by.

c) In a truly unconstrained system, the information can only be monitored and the system may react to it—it cannot be controlled.

This loss of control over data is one of the most difficult challenges in the prior art. The prior art clearly suggests that software consists of a 'controlling' program that takes in inputs, performs certain predefined computations, and produces outputs. Nearly every installed system in the prior art complies with this approach. Yet it is obvious from the discussion above that this model can only hold true on a very localized level in a UCS. The flow of data through the system is really in control. It is illustrative to note that the only example of a truly massive software environment is the Internet itself. This success was achieved by defining a rigid set of protocols (IP, HTML etc.) and then allowing Darwinian-like and unplanned development of autonomous but compliant systems to develop on top of the substrate. A similar approach is required in the design of unconstrained systems.

In the traditional programming world, a programmer would begin by defining certain key algorithms and then identify all of the key inputs into the system. As such, the person or entity supplying the data is often asked to comply with very specific data input requirements impacting the format, length, field definitions, etc. The problem with this approach, however, is that predicting needed algorithms or approaches that are appropriate to solving the problem of 'understanding the world' is simply too complex. Once again, the conventional approach of defining processing and interface requirements, and then breaking down the problem into successively smaller and smaller sub-problems becomes unworkable. The most basic change that must be made, then, is to create an environment that operates according to data-flow rules, not those of a classic control-flow based system.

In spite of the prevalence of control based programming frameworks, various data-flow based software design and documentation techniques have been in usage for many years. In these techniques, the system design is broken into a number of distinct processes and the data that flows between them. This breakdown closely matches the perceptions of the actual system users/customers and thus is effective in communicating the architecture and requirements. Unfortunately, due to the lack of any suitable data-flow based substrate, even software designs created in this manner are invariably translated back into control-flow methods, or at best to message passing schemes, at implementation time. This translation begins a slippery slope that results in such software being of limited scope and largely inflexible to changes in the nature of the flow. This problem is at the root of why software systems are so expensive to create and maintain.

At the most fundamental operating system scheduling level, we need an environment where the presence of suitable data initiates program execution, not the other way round. More specifically, what is needed is a substrate through which data can flow and within which localized areas of control flow can be triggered by the presence of certain data. Additionally, such a system would ideally facilitate easy incorporation of new plug-in control flow based functions or routines and their interface to data flowing through the data-flow based substrate so that it will be possible for the system to 'evolve'. In essence, the users, knowingly or otherwise, must teach the system how they do what they do as a side effect of expressing their needs to it. No two analysts will agree completely on the meaning of a set of data, nor will they concur on the correct approach to extracting meaning from data in the first place. Because all such perspectives and techniques may have merit, the system must allow all to co-exist side by side, and to contribute, through a formalized substrate and protocol, to the meta-analysis that is the eventual system output.

SUMMARY OF INVENTION

The present system and method provide such a system. To implement a data-flow based system, three basic components must be created and integrated:
  a) A data-flow based scheduling environment that balances the needs of data initiated program execution as a result of flows with other practical considerations such as user responsiveness, event driven invocation, user interface considerations, and the need to also support control-flow based paradigms where required.
  b) A visual programming language, based on the flow of strongly-typed run-time accessible data and data collections between small control-flow based locally and network distributed functional building-blocks, known henceforth as widgets.
  c) A formalized pin-based interface to allow access to data-flow contents from the executing code within the widgets.

The pins on the widgets include both pins used to control execution of a widget as well as pins used to receive data input from a data flow. The system and method further include a debugging environment that enables visual debugging of one or more widgets (or collections of widgets). Data control techniques include the concepts of "OR" and "AND" consumption thereby permitting either consumption immediately or only after all widget inputs have received the token. Additional extensions to this framework will also be described that relate to the environment, the programming language and the interface.

DETAILED DESCRIPTION OF THE PREFERRED EMBODIMENT

Figure 1:
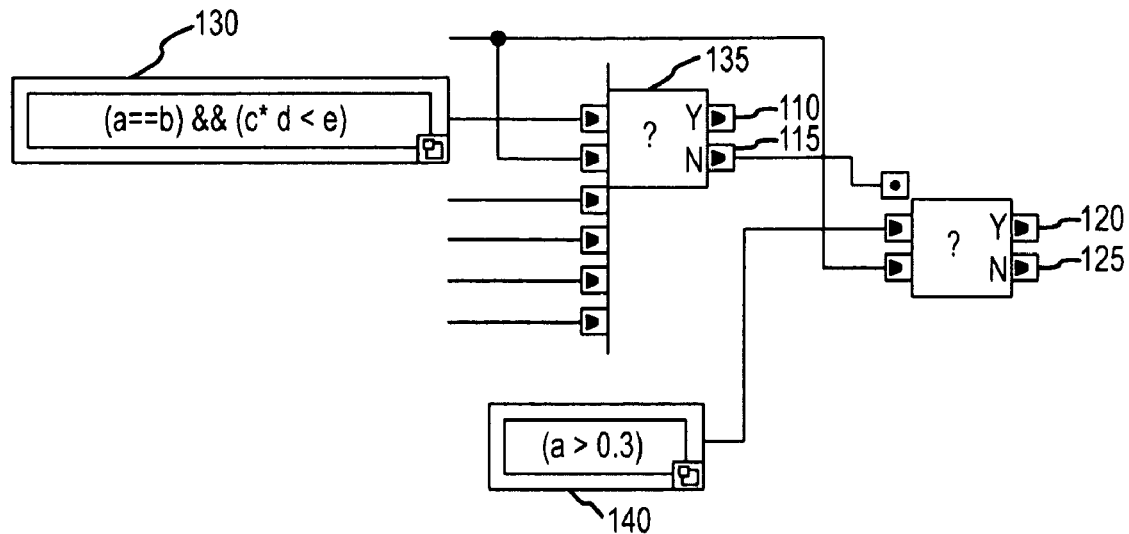
FIG. 1 illustrates an example of a conditional statement.

The system described herein may be used in conjunction with a number of other key technologies and concepts that represent the preferred embodiments of the present invention. These various building-block technologies have been previously described in the following patent applications attached hereto as Appendix 1, hereinafter referred to as "Memory Patent Application" now U.S. Patent Application Publication 2003/0182529 A1 and Appendix 2, hereinafter referred to as "Types Patent Application, now U.S. Patent Application Publication 2004/0073913 A1, both of which are incorporated herein by reference.

As set forth above, the system is preferably comprised of the following components:

The present system and method provide such a system. To implement a data-flow based system, three basic components must be created and integrated:
  a) A data-flow based scheduling environment that balances the needs of data initiated program execution as a result of flows with other practical considerations such as user responsiveness, event driven invocation, user interface considerations, and the need to also support control-flow based paradigms where required.
  b) A visual programming language, based on the flow of strongly-typed run-time accessible data and data collections between small control-flow based locally and network distributed functional building-blocks, known henceforth as widgets.
  c) A formalized pin-based interface to allow access to data-flow contents from the executing code within the widgets.

The requirements for and implementation of each of these required components will be addressed in the sections that follow. All of the structures defined and used below (widgets, pins, flows, constants, etc.) are preferably implemented within the flat memory model described in the Memory Patent and are contained within a loadable and executable memory allocation known as a 'view'. Only complete and correct views can be 'run' by the data-flow scheduler. There may be any number of different views in the system, and any number of instances of a given view.

As an initial matter, it is helpful to describe the "building blocks" involved in the present invention. A 'widget' is the fundamental building block of the system. A widget contains certain functionality encapsulated along with a definition of the inputs and outputs necessary to interface to that functionality. An atomic widget contains compiled code that generally cannot be either examined or altered within the framework of the environment. A compound widget contains an inner structure that defines any subordinate widgets that are required to implement the required functionality, together with the data flows between these contained widgets. In general compound widgets can be opened, examined, and altered by system users. Compound widgets may themselves be combined with other widgets (both atomic and compound) to yield higher-level compound widgets, to any arbitrary level of nesting. At the uppermost level, widgets are combined into 'views' that may be thought of as complete mini-applications that preferably include all necessary UI functionality.

It is the views, and the widgets that they contain, that are loaded into the environment at execution time. Thereafter, the widgets are scheduled and executed according to the control and data flows defined in the widgets themselves. Atomic widgets can be grouped into functionally related sets known as widget packs.

In the preferred embodiment, widget packs appear and are manipulated in the Widget Editing Mode (WEM) diagram as a single unit, but each of the members of the unit can be executed independently of the other members. The principal functional member of a widget pack (i.e., the 'do it' function) is known as the formal widget, and all other widgets in the pack are degenerate (known as degenerate widgets). The pack metaphor is necessary to support asynchronous access to elements or attributes of the internal state of a logical functionality implemented by the pack. Without packs, data-flow is essentially a synchronous metaphor where widgets do not run until all necessary inputs have arrived. The support of 'exclusive' pins (described later) is another exception to this rule.

Compound and atomic widget inputs and outputs as displayed during WEM, are collectively referred to as pins. A formal pin is one that must be connected in order for the widget to operate correctly, a degenerate pin need only be connected if required in the particular use of the widget and may otherwise be left unconnected. Degenerate pins come in two varieties; those that assume a default value within the widget when unconnected (defaulted degenerate pins), and those that do not (un-defaulted degenerate pins).

A View has associated with it a specialized compound widget known as a view widget which contains a collection of atomic or compound widgets, each of which may have at most one user interface region known as a pane. These regions range from buttons, windows, controls, etc. to arbitrarily complex closed shapes. In addition to the view widget, a view contains the layout information that specifies the arrangement of display panes within the enclosing window. The entire view is enclosed in a view window. The system is capable of accessing and transferring between large numbers of different views both under menu control, and by use of suitable view change widgets. Like widgets, views may be shared between users or may be unique to a particular user. Like other widgets, view widgets may have data flow inputs and outputs, but in the case of views, these are physically mediated by network events/messages that are sent to or received from other views, either in the same workstation or another node on the network. A data-flow environment built on this metaphor is thus transparently distributed.

It is possible to execute a widget without making connections to any degenerate inputs or outputs that a widget contains; in this case the default values (if specified) will be used for the inputs, and the output(s) will be discarded. If no default is defined for a degenerate input, then within that widget, no tokens will appear from that input pin and hence any widgets connected to that input cannot become eligible for scheduling. Degenerate widgets I/O pins and the defaults associated with them can be explicitly overridden by connecting the inputs to an appropriate source/sink of the type required. Default values can be read and edited as part of the widget editing process. The interface provides a semi-automated and convenient method of resolving type conflicts and inserting the appropriate type conversion widgets. Type conversion widgets generally have many degenerate inputs and outputs, each of which will interface to a particular type. The interface is able to recognize type conversion widgets for what they are (via a dedicated flag), and when a type conflict occurs, searches all available type converters for those that meet the necessary input and output criteria. When all suitable type converters have been identified, the user is able to select the most appropriate from a list of all converters that meet the criteria.

Widget data-flow inputs and outputs can be connected to other data-flow inputs and outputs (of a compatible type) in widget editing mode (WEM) in order to define the required widget functionality. For example, a single widget data output can be connected to multiple data-flow inputs. When a multiple input connection is made to a single output, the interface allows the user to choose whether the output is consumed by the first widget that has all inputs available including the input in question (OR consumption logic), or whether it is only consumed when all connected widgets have run (AND consumption logic). Conversely, multiple widget outputs can be connected to a single widget input, in which case the input accepts and consume each widget output as it becomes available. This situation occurs commonly in user control panels where a number of buttons effect the state of a single widget/display. It is possible (though uncommon) for multiple widget outputs or sources to be connected to multiple widget inputs or sinks. This capability may be important for widget mediated load sharing across multiple server processes, for example.

Every widget has the potential to accept a single control flow input and to generate a single control flow output; these pins are degenerate (i.e., are ignored unless actually connected). In the preferred embodiment, control pins cannot have defaults associated with them. Like data-flow inputs and outputs, control-flow pins can be wired up to other control flow pins, but not to data flow pins (unless of Boolean type). Control flow wiring carries an implicit Boolean value indicating that the control flow criteria concerned has or has not been met. If the control flow condition has not been met, then control flow wiring carries the value false, and does not trigger any connected control flow inputs. If the condition has been met, the wiring carries a true value and triggers any connected control flow inputs. Unless explicitly altered within a widget definition, a widget's control flow output goes true immediately upon completion of execution of that widget, it goes false immediately after execution of the widget begins. If a widget's control flow input is connected, then execution of that widget cannot begin until the control flow signal to which it is connected is asserted. Normally, it is likely that compound widgets can be constructed entirely based on data flow programming and without the explicit use of control flow pins. However, there are a number of situations, especially those involving the synchronization of multiple server processes, which may require use of the control flow pins. The system also permits a tie between multiple control flow outputs and a given control flow input in which case the associated widget cannot begin execution until all data flow inputs are satisfied and, either the AND or the OR of all control inputs is asserted (depending on the type of control input used). Selection of either a control flow OR/AND for a widget control flow input is generally performed when connecting control flow signals. The system also supports connections between a single widget control flow output to multiple different control flow inputs. In this case, all widgets whose inputs are so connected cannot execute until the control flow output is asserted. Unlike data-flow connections, control flow signals are not 'consumed' by the receiving input pin, but remain asserted until source widget activity drives them false. This means that, in general, control flow signals can be multiply sourced and synced without the potential for confusion as to what will happen. In the preferred embodiment, all logical operations on the control flow signals are the responsibility of the engine/interface; this knowledge does not propagate into the widget itself. It is possible to connect a control flow signal or pin to any data flow signal of the system defined type Boolean; connection to any other data flow type is generally forbidden.

The degenerate widgets of a widget pack are capable of accepting and producing both formal and degenerate data flow I/O pins as well as the standard control flow pins. Individual members of a widget pack can be invoked independently of other members of the pack but all members of the pack share the same storage area; this storage area is allocated at the time the widget pack is instantiated (generally via the initialize entry point of the formal widget), and is passed by reference to each member of the pack as it is invoked by the engine. As with all other widget types, a degenerate widget of a widget pack only executes when all of its inputs become available. Degenerate widgets need not provide any entry points other than the 'execute' entry point, the engine invokes the entry points associated with the formal widget of the pack when using entry points other than execute. All widgets of a widget pack are stored together in a single file and for the purposes of copying and other activities using the WEM menus are treated as a single unit. It is generally not possible to treat a degenerate widget of a pack as if it were a fully defined atomic widget within the normal WEM environment.

Within a pack, the various members can communicate with each other via the data area and can also directly invoke other members of the pack. As a result, it is valid for degenerate widgets of a pack to contain nothing but outputs which are presumably produced when the internal state of the pack meets certain criteria.

A View can be thought of as a mini application, whose functionality is defined by the widgets it contains and the data flows between them. A view's appearance is most easily defined by superimposing the display components of all widgets in the view on a background that is an image. Views provide the framework within which it becomes possible to instantiate and execute the various atomic and compound widgets. No widget can execute unless it is either explicitly or implicitly contained in a view. Views are preferably stored in view definition files which may be accessed and initiated via the environment's view menu. Each view definition file contains as a minimum the following components:

A specialized compound widget (a view widget) associated with the view that defines the control and data flows between the widgets that make up the view Layout information describing the size of the view window, and the location, shape and size of all display and user interface components within that window an image that describes the background for the view.

Views may be in one of two states: active or inactive. An active view is one that is currently executing and has therefore loaded all contained widgets into the engine where they are currently executing. An inactive view contains no executing widgets and is not currently loaded into the widget engine. Every view has associated with it a window which may or may not be visible at any given time. For the purposes of this description, the view that is associated with the front window on the user's screen is known as the front view and only one view can be the front view at any given time. This would not necessarily be the case in alterative display environments that permit 2+ dimensional views, however. Unlike widgets, views are generally not nested within (in a visual sense) other views. A view is always the outermost component or container for a given user defined functionality and usually has no relation to the current screen position of any other view. Views also can be combined into groups called view packs and these views packs share a logical context much in the manner of widget packs.

As set forth above, a view has associated with it a compound widget defining the data and control flows between the display and functional widgets that go to make up the view. This compound widget is known as a view widget and is similar to any other compound widget. Because it is part of a view, however, its data flow I/O pins are connected to other views by means of network events. The majority of view widgets will have zero inputs and outputs. Certain specialized views, however, may be controlled from other views and in such cases the controlling view will have data flow outputs while the controlled view will have corresponding data flow inputs. View outputs may also optionally include a target view and network node in order to route the event to the intended destination. If no such qualifiers are included, the event will be sent to any views in the local environment that contain inputs whose name and type exactly match that of the view output. If no such inputs exist, the data flow output is discarded. Unlike other widget types, a view widget is scheduled (or rescheduled) whenever any of its inputs becomes available. Internal scheduling of the view, however, may be suspended should other required inputs still be undefined.

Any component of a view widget may also have (one or more) panes associated with it. In such cases, the view causes a marquee or image of that pane to appear in the view layout window where it may be re-sized (within limits) and relocated as part of the view layout process. Panes are normally rectangular but it is possible to create and interact with panes that occupy any arbitrary closed region. A view may be comprised of many panes, each of which represents the display region of the widget responsible for interpreting or displaying the control/display that the pane relates to. For widgets whose appearance is fully determinable at layout time (e.g., named buttons), the final widget appearance is shown in the pane during view layout.

As described above, the WEM window provides the interface in which views and widgets may be edited, modified or displayed. For example, within the WEM window, the subordinate widgets and the data flow between them is displayed. In the preferred embodiment, colored lines that join the pins of widget icons/symbols to other pins in the diagram represent data flow. The color of the line can be used to convey type information. Wherever one or more lines in a WEM window is joined in terms of data or control flow, this is represented by a standard line junction symbol. By default, data-flow outputs are consumed when the widget associated with every connected input has been triggered. The user has the option to select that the output be consumed when the first widget that has a connected input is triggered. These two forms of signal consumption logic are referred to in this document as "OR consumption" (first triggered widget input consumes output) and "AND consumption" (output is only consumed when all widgets with triggered inputs have been run). Different forms of data flow output consumption logic may also be implemented by the scheduling engine. Control flow signals are never 'consumed'. They remain asserted until renewed widget activity causes them to go false. There is an implicit latch on every widget data input so that regardless of the consumption logic operating outside the widget, within the widget, the input may operate using either OR/AND Consumption, the default is AND Consumption. When multiple data-flow outputs are connected together to one or more data flow inputs, the same consumption logic applies to all connected widgets. During execution, a second output value will not be applied to the interconnect signal by the engine until any previous output has been consumed, thus forming an automatic queuing mechanism.

The representation of various standard programming constructs (such as the loop, switch, and conditional statement) are also supported within a WEM window. For example, the conditional statement (i.e., if then) is provided by an atomic widget that accepts a string defining an arbitrary expression in terms of the widget inputs that resolves to a Boolean value either directly (because all inputs are Boolean), or as a result of use of a comparison operator within the expression. This atomic widget has two degenerate outputs which are automatically displayed when the widget is placed. The first corresponds to the YES condition, the second to the NO condition. The conditional widget only generates one or other degenerate outputs when it runs. As a result, any data flow connected to the un-generated output will not be executed. The conditional widget has a single formal input that accepts the Boolean expression, and a large number (up to 26) of degenerate inputs each of which will accept any scalar numeric value or a derived type. Each connected degenerate input can be referred to in the expression by its lower case letter or signal name.

Referring now to FIG. 1, an example of a conditional statement is shown. In this example, a compound conditional statement of the form: "if (a=b) && (c*d<e) then . . . else [if (a>0.3) then . . . else . . . ]" is provided. Because the outputs 110, 115, 120, 125 of the conditional widgets are both degenerate, either the 'then' clause or the 'else' clause may be omitted simply by not connecting the corresponding output 110, 120. This gives the user the freedom to create any conditional statement that he wishes simply by combining simple 'if' blocks as desired. Note also that if the user simply wanted to connect a widget that did not expect a Boolean parameter as input to either the then or the else clause of a conditional widget, he can do so simply by connecting the Boolean output from the conditional widget to the control flow input of the widget required. This is because, in the preferred embodiment, control flow pins may be connected directly to data-flow signals of the system supplied type Boolean. Since control flow inputs are only triggered when a Boolean true value exists, any widget thus connected will only run when the appropriate clause is satisfied. In example illustrated in FIG. 1, the else clause of the first conditional widget 130 will produce no output unless the first condition is met when it will output a true value. This means that the expression "a && (b>0.3)" 140 is not required in the negative case since the widget 135 will not even run unless condition 130 is true.

The case or switch construct is provided by an atomic widget that takes as input two values. The first value is a comma-separated list of constant integer expressions (includes characters) or ranges, the second is an integer value to be evaluated against the list. The output of the case widget is a variable number of degenerate Boolean outputs (each of which preferably represents one of the case conditions being satisfied) and the first of which is always the default case (i.e., no other condition satisfied). Only one case widget output will be generated on any given execution of the widget, and as for the conditional widget, it outputs the Boolean value true. If no specified condition is met then an output will be produced on the default pin.

Figure 2:
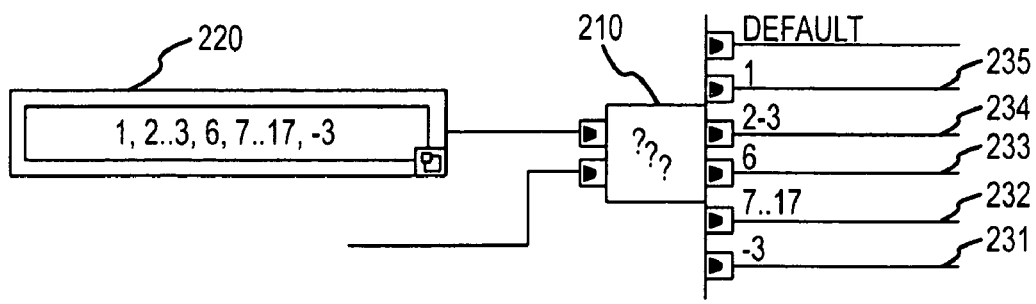
FIG. 2 illustrates an example case statement using an atomic widget.

Referring now to FIG. 2, an example case statement using an atomic widget is shown. In this example, the case statement within the widget 210 evaluates the integer input 220 against 5 different values or ranges. Only one of the outputs 231, 232, 233, 234, 235 will be generated as a result of widget 210 execution. This is true even if more than one condition is met due to overlapping ranges. When ranges for a case widget overlap, only the first condition in the list to be satisfied will cause an output. First, in this case, would be represented by going from top to bottom among the outputs 231, 232, 234, 234, 235. Because case widget outputs behave identically to conditional widget outputs, they can be used to trigger other widgets via their control input pins in the same manner described above for the conditional widget. The interface preferably prevents the user from connecting different inputs of a downstream widget to signals that are directly or indirectly connected to different output pins of either a conditional or a case widget within the WEM window. This is because, since only one such pin can be triggered by definition, any downstream widget that relies on more than one such widget output, will by definition never execute. This condition is normally enforced by the block structure of standard programming languages but since, in a visual environment, this structure may not be so apparent, block structuring is preferably enforced by the WEM environment. In the visual environment, the outputs of a case widget may be automatically labeled with the case value. This feature is depicted in the diagram above with respect to outputs 231, 232, 233, 234, 235. The WEM interface is also capable of highlighting all widgets and connections that are 'downstream' of a given selection in the WEM diagram by special UI actions.

The WEM interface would also preferably prevent the user from connecting a data flow output of any widget (A) to any data flow input of a second widget (B) that either directly or indirectly is required to run in order for the widget (A) itself to become eligible to run. This requirement is made in order to prevent the user from accidentally setting up data flow diagrams that have hidden loops in them that mean they will not execute (or will always execute). Note that this requirement by itself makes it impossible to construct the 'loop' programming construct using pure data flow connections and widgets not expressly designed to implement loops. Loop constructs generally require the use of a variable to pass values from one loop iteration to the next. Once initialized, the variable value is always available and hence removes the possibility of creating a data flow input condition that cannot be satisfied. When a user attempts to create a data flow dependency loop in WEM mode, he is preferably warned of this fact and given the opportunity to create a variable that removes the disallowed dependency. In the event that a data or control flow input pin is multiply sourced, and one source is not dependent on execution of the widget concerned, then it is permissible to connect a downstream widget output to this widget input pin. There are a number of problems associated with loops that make them difficult, if not impossible to implement in a data flow design without enforcing block structuring (i.e., putting the loop body within a compound widget), these are:

No data flow output can be tied back to a widget that appears earlier in the loop (including the same widget that produces the output) without creating a situation where neither widget can run because each depends on the other to trigger them (known as a deadly embrace).

A data flow signal that comes from code lying outside the loop cannot be directly connected to a data flow input within the loop because the loop may execute many times and will therefore consume the input on the first pass and then hang up.

A data flow output that comes from code lying inside a loop cannot be directly connected to a data flow input lying outside the loop because the loop may execute many times and will therefore produce a series of outputs which will either unintentionally trigger the widget outside the loop on each pass, or more likely, if the widget outside the loop requires other non-loop inputs, will have to be queued up waiting for access to the data flow signal. It is probable that such a behavior would overload any queuing mechanism provided by the engine to handle multiply connected outputs since such a queue only needs to be as big as the number of connected outputs.

It is visually very difficult to display the loop concept at a single level so that it is immediately obvious what is, and what is not part of the loop.

For the reasons described above, loops are implemented by one or more system supplied compound widgets that provide a number of degenerate universal input and output pins for passing data of any type into and out of the loop body and which allow specification of the loop behavior.

A suggested set of widget scheduling rules to be enforced by the engine is given in the table below. Many of these rules appear throughout the text above but they,are summarized and augmented here in order to make the full rule set more apparent. The term widget is used below to imply both atomic widgets and compound (or view) widgets. When a distinction is required, the particular widget type is explicitly stated. The term signal is used below to refer to either a control flow or a data flow. Where a distinction is required, the type of signal (control or data) is explicitly stated. The term token is used below to refer to a data flow signal to which a value has been written, but has not yet been consumed. A linear compound widget is defined as a one that does not include any explicit connection to the control flow output. A cyclic compound widget is defined as a one that includes an explicit connection to the control flow output and which therefore may include explicit loops. A descendant widget Z of an ancestral widget Y within an enclosing compound widget X is defined as any widget within the WEM diagram for X that either directly or indirectly depends on data or control flow outputs from Y in order to become eligible for scheduling. Z is a formal descendant widget of Y if the dependency between Y and Z is mediated by signals connected only to formal widget outputs. Z is a degenerate descendant widget of Y if the dependency between Y and Z is mediated by at least one signal connected to any intervening degenerate widget output. The various descendancy terms described above may also be applied to the data or control flow signals attached to the widget Y. A pure data flow signal is defined as one that is not attached to a variable or constant symbol. A pure descendant data flow is one that can be traced back to a given ancestor through pure data flow or control flow signals alone.

| Scheduling Rule |
| --- |
| A widget is eligible for scheduling only when all of its connected data flow inputs have a token associated with them. A view may be scheduled whenever any of its data flow inputs have a token associated with them but may subsequently 'hang up' should other inputs be required and still be undefined. |
| If a widget has an explicit connection to its control flow input pin, then that widget (and any widgets it contains) is only eligible for scheduling when the value of the control flow pin is set to TRUE. This applies even if the widget is compound and has already started execution. (i.e., you can single-step a compound widget to any nesting level simply by explicit control of the highest level control pin). |
| Execution of a linear compound widget (and all widgets called by it) completes when all of its connected output pins have data tokens associated with them (i.e., have been assigned a value). |
| Execution of a cyclic compound widget (and all widgets called by it) completes when the control output pin is driven TRUE by the control or data flows within the widget. The implementation may encapsulate this functionality so that for standard loops, the user is unaware of the control pin connection. |
| Once a widget has been scheduled for execution, it cannot again become eligible for scheduling until execution completes. |
| If a widget input is specified as 'only on update' then that widget only becomes eligible for scheduling each time a value is written to the data flow signal connected to that input. This applies even if that signal has an un-consumable token associated with it (see below). If multiple values are written to the input signal before the connected widget is scheduled, it is scheduled only once in response to the series of updates. |
| The following signals have tokens associated with them that cannot be consumed: |
| 1) Any signal that is connected to a variable symbol once that variable becomes valued. If that signal is also attached (within the compound widget) to a variable symbol, then the input value may be overwritten by subsequent widget action. Variable values once written, persist across multiple executions of the same widget in the same context |
| 2) Any signal that is connected to a constant symbol. |
| 3) Any signal that is directly connected to a widget control flow output. |
| 4) Any signal that is directly attached to a connected or defaulted data flow input of a compound widget. |
| A pure data flow that is specified as AND consumption logic (the default during construction), causes any tokens associated with that flow to be consumed only after all widgets that have input pins connected to that data flow have been scheduled and executed. If multiple widgets have input pins connected to the pure data flow signal in question, then each may be scheduled only once as a result of any given token appearing on the signal even if that token remains unconsumed. |
| A data flow that is specified as OR consumption logic (during construction), causes any tokens associated with that flow to be consumed by the first widget that has an input pin connected to that data flow, and which is scheduled and completes. |
| For a linear compound widget, the engine drives the control output pin FALSE at the time the widget is first scheduled, and TRUE when widget execution completes. |
| A trash can symbol will immediately consume any tokens associated with the data flow to which the trash can is attached (even if other widget input pins are also attached). Trash cans may not be attached to any signal which by definition cannot be consumed. |
| Within any compound widget X, once a widget Y has been scheduled and executed, it cannot become eligible for scheduling again while any unconsumed token remains on a pure descendant data flow signal. |
| Any widget whose output is attached to a multiply sourced pure data flow signal that currently has a token associated with it, can be scheduled and executed (but not completed); the engine will not write any new token(s) produced by that widget until the pre-existing token on the backed-up output data flow signal has been consumed, nor will the engine permit the control flow output to go TRUE until this is the case. Furthermore, the widget (and any widgets it contains) is no longer eligible for scheduling and execution regardless of tokens appearing on its inputs, until the engine has transferred its previous output tokens onto the relevant data flow signals. |
| If a widget Y within a compound widget X is identified as an 'as needed' widget (for example a dialog widget) then in addition to any other rules that might apply, that widget will not be scheduled or executed until its output is required in order to cause another widget within X to become eligible for scheduling. |

| Scheduling Rule |
|---|
| Any widget Y within a compound widget X whose outputs are exclusively connected directly or indirectly to unconnected degenerate outputs of X (or to a trash can), will not be scheduled or executed regardless of tokens appearing on its inputs. Furthermore, the widget Y is not considered in any consumption logic applicable to signals connected to its input pins. To all intents and purposes Y is completely ignored in all scheduling activities related to X. This rule can be enforced at load time, it is not dynamic. |
| Any widget Y within a compound or view widget X, and which has zero connected inputs, never becomes eligible for scheduling or execution. To cause such a widget to execute, its control input pin must be driven true by connecting it either directly to the control input of X or to another Boolean signal within X. |
| Once any widget Y has been scheduled and executed within an enclosing widget X, it is automatically moved to the last position in the scheduling check sequence so that in addition to all scheduling rules outlined above, the widget Y is not even checked again for scheduling eligibility until every other widget with in X has been checked on a subsequent pass. |
| All rules described above apply equally and simultaneously to every level of a view and the various subordinate compound widgets that it calls to any arbitrary level of nesting. Scheduling of the various components of each nested WEM diagram occurs independently of other levels except that each nested compound or atomic widget must complete before its output signals become available at the next higher (calling) level and thereby potentially cause one of the rules described above to be triggered at the higher-level. |

While the illustrated widgets give the appearance of passing widget inputs by value, for efficiency reasons the implementation (wherever possible) passes widget inputs and outputs by reference, not by value. Pass by value is only required in cases where the widget input is overwritten within the widget itself (by use of a variable symbol), and the signal is not simultaneously attached to a formal widget output within the WEM diagram. Because of the scheduling rules described in the table above, the internal values of any inputs to a widget that are supplied by pure data flow connections cannot change during the period of execution of that widget. Preferably, inputs that are externally attached to a variable symbol may potentially change during widget execution.

While the table given above describes the rules that relate to scheduling and execution within a particular context, it is important to understand that simultaneously there may be many active views, all of which are being scheduled and executed. This gives rise to a number of considerations with regards to prioritization between the various views that are illustrated in the scheduling algorithm.

The scheduling algorithm forms the core of the system architecture in that all system functionality, at some level or another, is initiated as part of a view launched within the scheduling environment (referred to as the 'widget engine'). The WEM user interface, including widget building and view editing, can be thought of as a separate application from the scheduling process itself, and could be replaced with other user interfaces without changing the widget engine itself. The widget engine is a strongly-typed data flow interpreter which can read in and subsequently execute atomic and compound widgets together with the data structures that define their I/O needs and characteristics.

Figure 3:
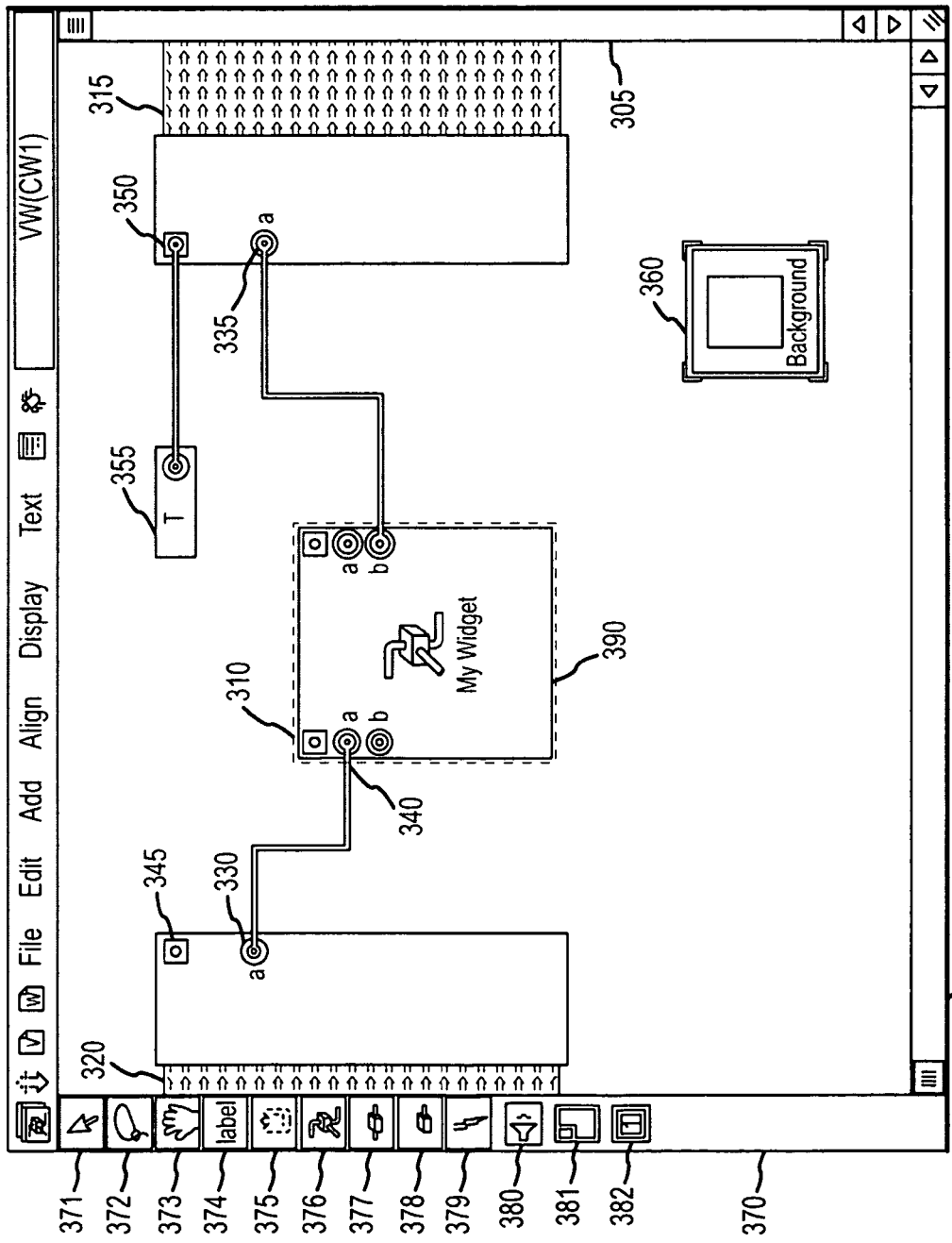
FIG. 3 illustrates a sample embodiment of a Widget Editing Mode (WEM) window 300.

Referring now to FIG. 3, a sample embodiment of a Widget Editing Mode (WEM) window 300 is shown. In the illustrated example, the window 300 is a standard, titled, resizable window with scroll bars 305. The window 300 is used to define and edit data-flow functionality by connecting and configuring widgets 310. The two blocks 315, 320 connected by arrows to the edge of the window are the input and output bar of the compound widget being viewed. In this example, a single degenerate input 330 and single degenerate output pin 335 have been defined for this compound and connected to an embedded compound 310. In the preferred embodiment, this example could be created simply by clicking on the pin 330, dragging to the destination pin 340 it is to be connected to, and setting the type. The specialized pins 345, 350 at the top of the input 320 and output bars 315 are the control input pin 345 and control output pin 350 respectively. In the preferred embodiment, their type is always equivalent to 'Boolean'. As this diagram illustrates, the control output pin is wired to the constant 355, in this case true, which will enable the contents of the compound widget to run. The background widget 360 is a pre-supplied atomic widget serving the specialized purpose of defining the background visual appearance of the associated window. In this embodiment, the tool bar 370 provides (starting from the top):

The arrow tool 371 is used as a toggle switch to turn options on/off, or it simply selects items.

The lasso tool 372 can select freeform areas by clicking down and selecting the section.

The hand 373 moves the entire contents of the WEM window in different directions.

Label 374 can place a label on any element in the WEM window.

The clipboard 375 is activated when information is copied or cut to the clipboard. Select it to use as a paste tool when clicked at the paste position.

Click the widget tool 376 to insert a new compound widget.

Click the variable input tool 377 to insert a variable.

Click the constant input tool 378 to insert a constant.

Use the lightening bolt tool 379 to delete elements in the window.

Select the speaker 380 to set the volume.

Window size boxes 381 allow enlarging of the window. The default setting is one white square. This setting will not allow the window to be enlarged further than a few inches. The available settings permit expansion of the window vertically, horizontally, or both ways.

Grid tool 382 can be used to select to set the grid to which all data flow lines and objects snap in the window. It is possible to move a selected item from 1 to 8 pixels at a time.

Figure 4:
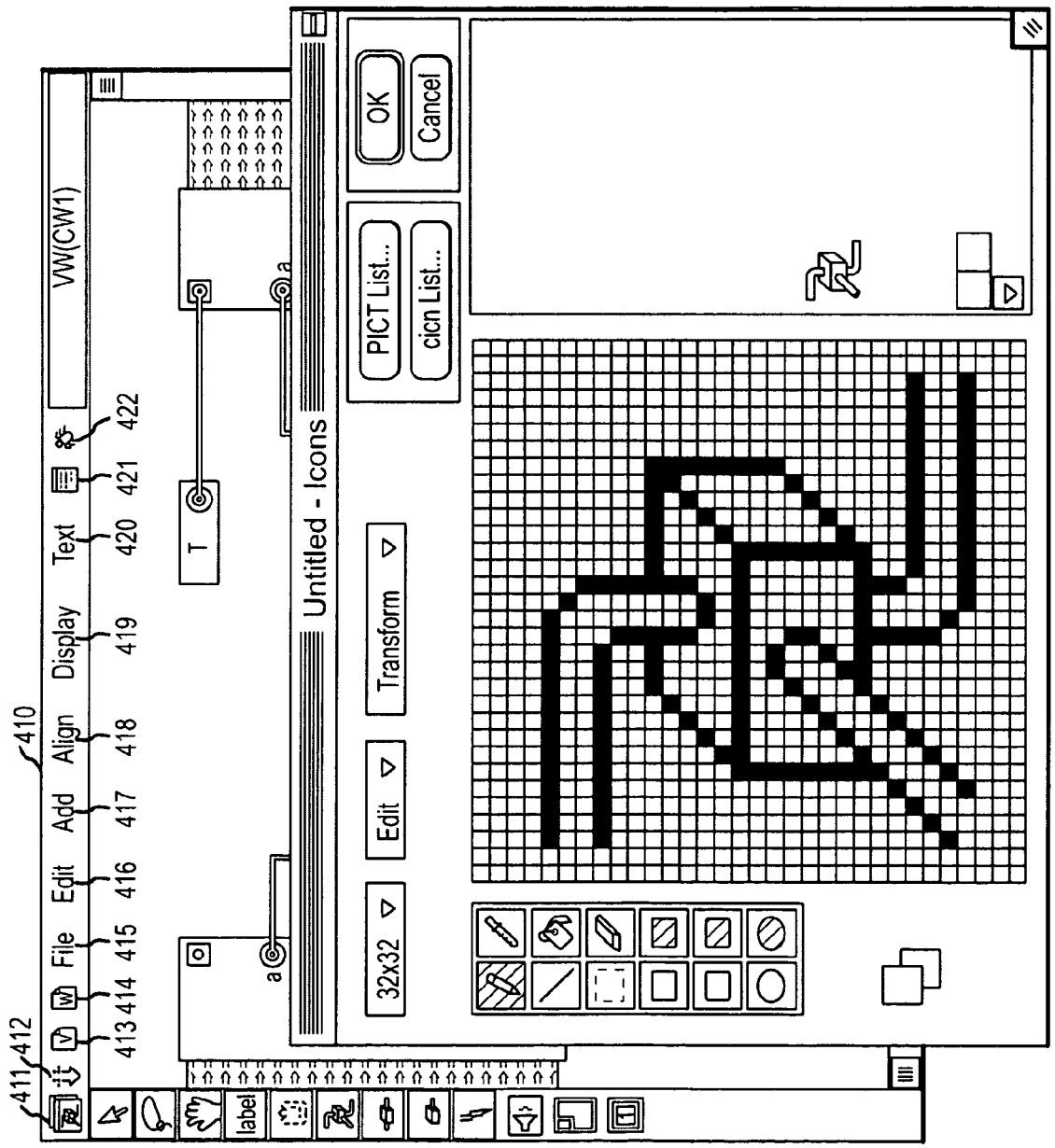
FIG. 4 illustrates a full-featured icon-editor that allows alteration of the widget icon.

Referring now to FIG. 4, a full-featured icon-editor that allows alteration of the widget icon is shown. In this example, the result of double-clicking on the icon 390 in the FIG. 3 is shown.

In the illustrated embodiment, a menu bar 410 is provided which provides an interface to a set of unique tools. Working across the menu bar at the top of the window (from left to right):

The view-pack menu 411 allows navigation between various members of a view pack in order to allow single session editing of the entire pack/report.

Once widgets are created within widgets, it is possible to move up or down the widget hierarchy with a up/down menu item 412.

The view menu 413 allows navigation and selection of any view stored on disk.

The widget menu 414 allows selection of any widget stored on disk

Figure 5:
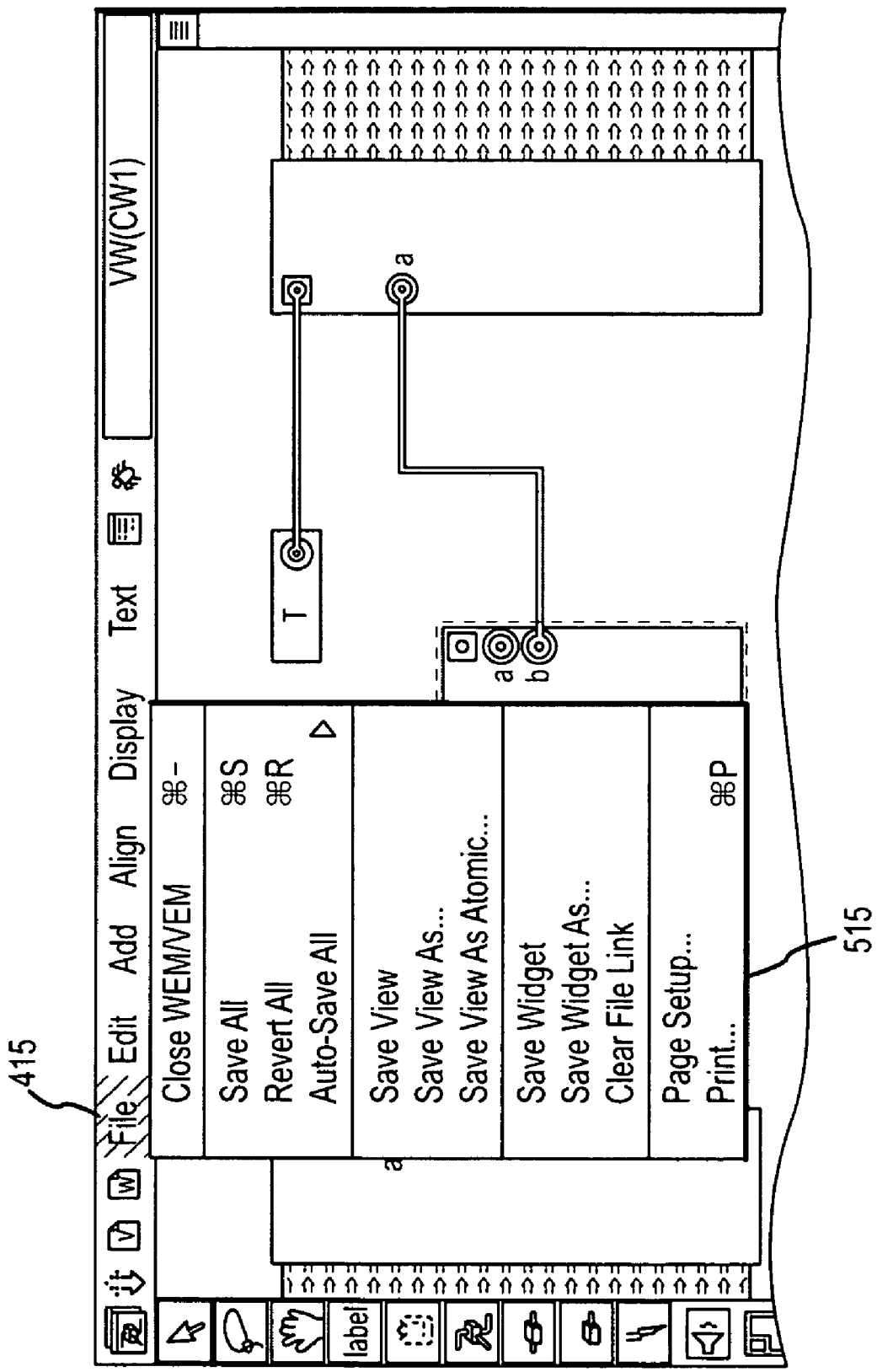
FIG. 5 illustrates a sample embodiment of a file menu 415 of the WEM.

The file menu 415 allows standard save/load type actions to/from disk. A sample embodiment of a file menu 515 of the WEM is provided in FIG. 5.

The Edit menu 416 is a standard Edit menu much like that found in any other application.

Figure 6:
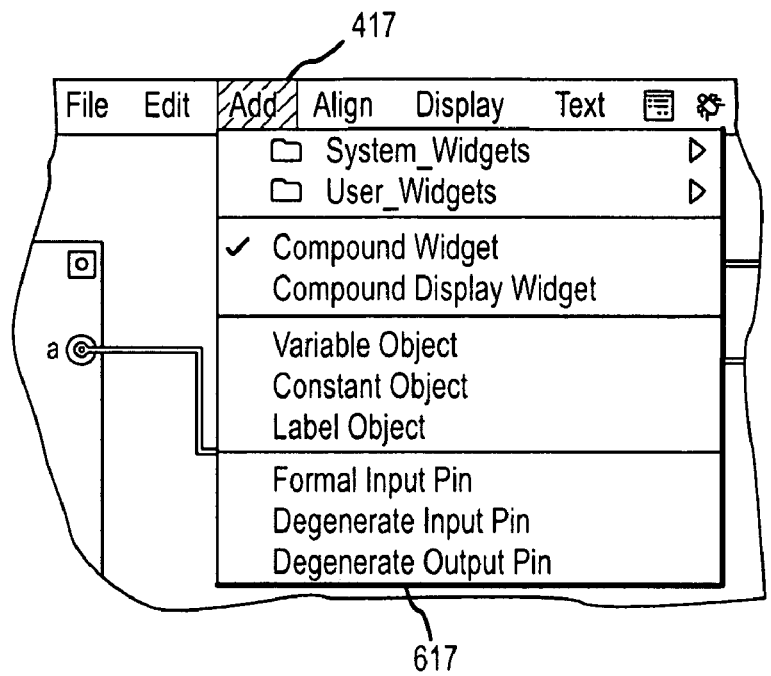
FIG. 6 illustrates a sample Add menu 417 of the WEM.

The Add menu 417 allows new widgets to be chosen and added as well as allowing the addition of other objects in the WEM diagram. A sample Add menu 617 of the WEM is illustrated in FIG. 6. In this example, a compound widget is selected.

Figure 7:
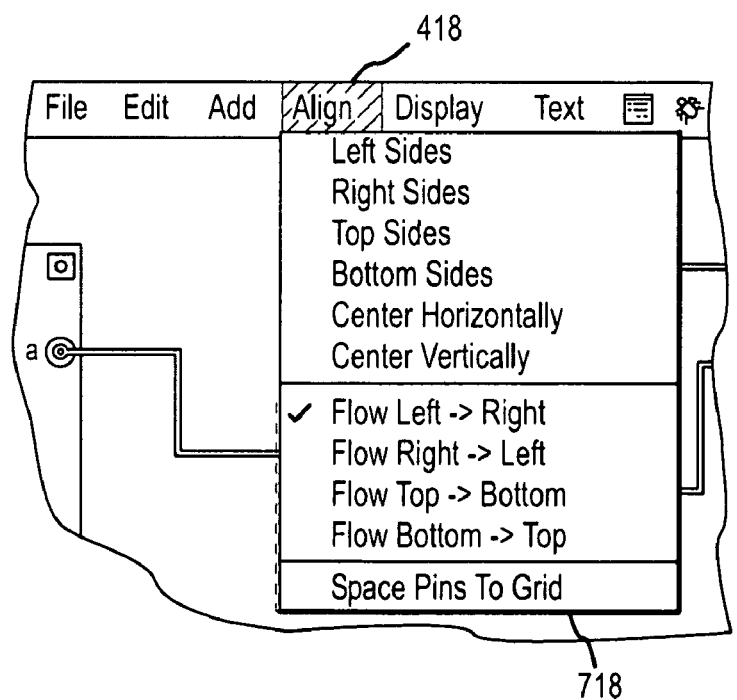
FIG. 7 illustrates a sample Align menu 418 of the WEM.

The Align menu 418 allows various aspects of the WEM diagram internal alignment to be configured. A sample Align menu 718 of the WEM is illustrated in FIG. 7. In this example, the flow selected is "Flow left->right".

Figure 8:
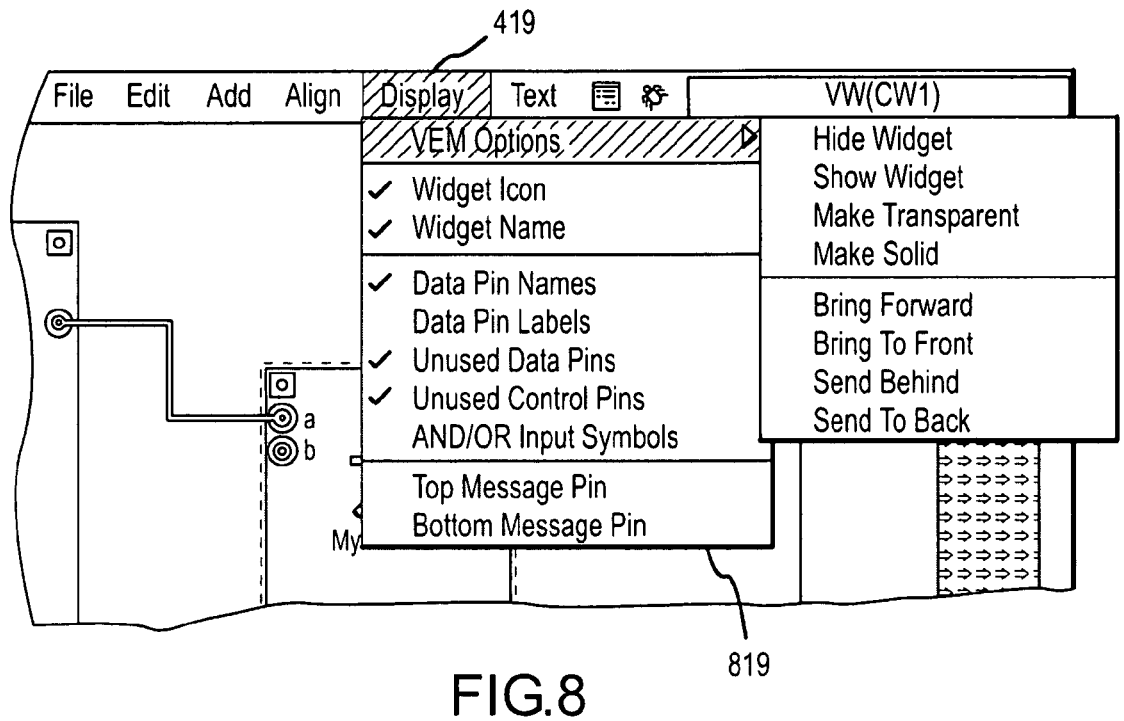
FIG. 8 illustrates a sample Display menu of the WEM.

The Display menu 419 allows various visual components of the WEM diagram and its contents to be configured as far as their appearance in the diagram is concerned. A sample Display menu 819 of the WEM is illustrated in FIG. 8. In this example, the sub menu "VEM Options" is selected.

The Text menu 420 provides standard control over text appearance such as color, style, font, size, etc.

Figure 9:
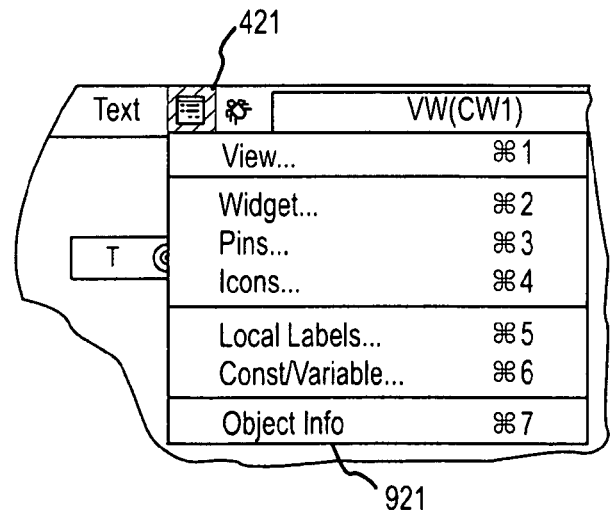
FIG. 9 illustrates a sample setup menu 421.

The Setup menu 421 allows access to a number of additional 'daughter' windows that can be used to examine and edit the details of the various types of objects in the WEM diagram. A sample setup menu 921 is illustrated in FIG. 9.

Figure 10:
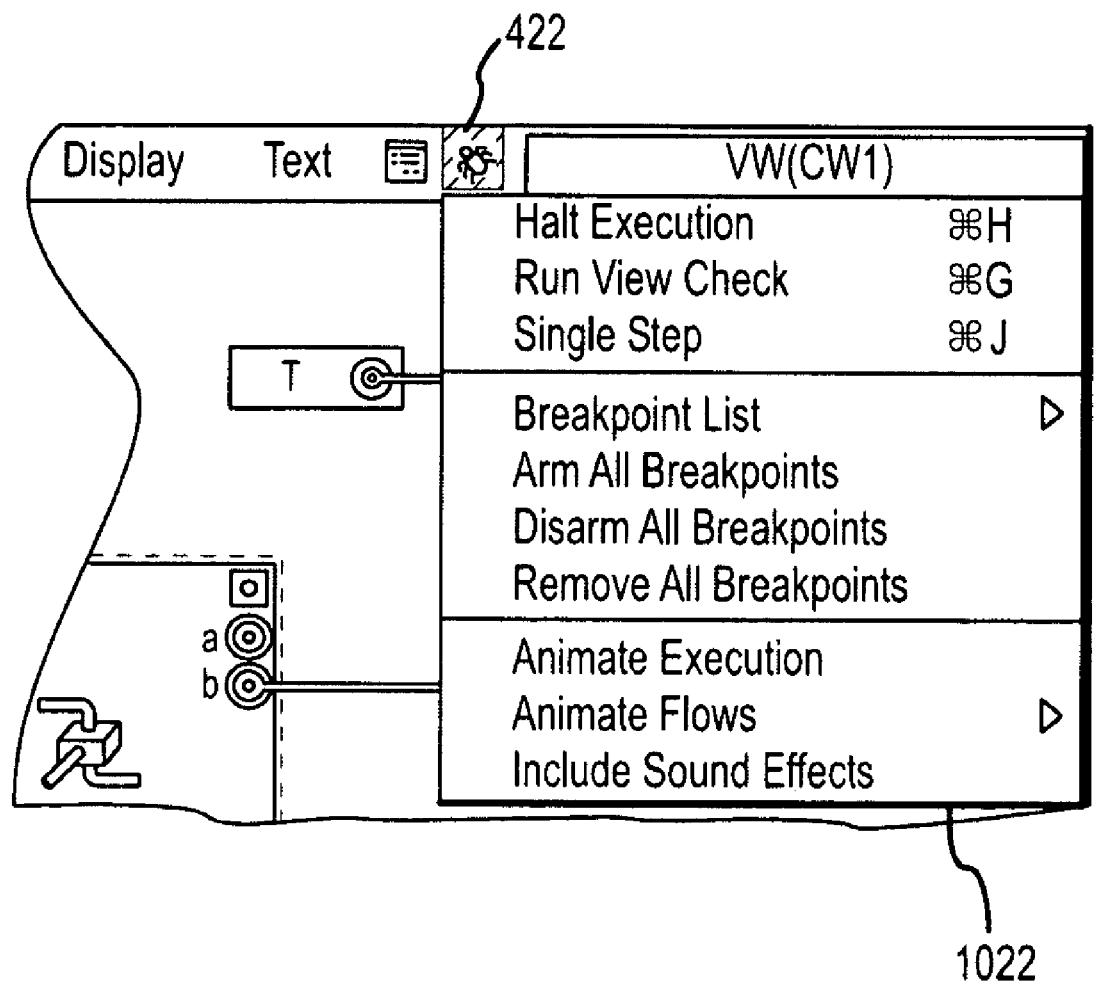
FIG. 10 illustrates a sample embodiment of the debug menu 422 of the WEM.

The Debug menu 422 is used primarily during run-time debugging of widget execution and allows examination of the state of all flows, widgets and pins and the tokens and data on them. A sample embodiment of the debug menu 1022 of the WEM is provided in FIG. 10.

Figure 11:
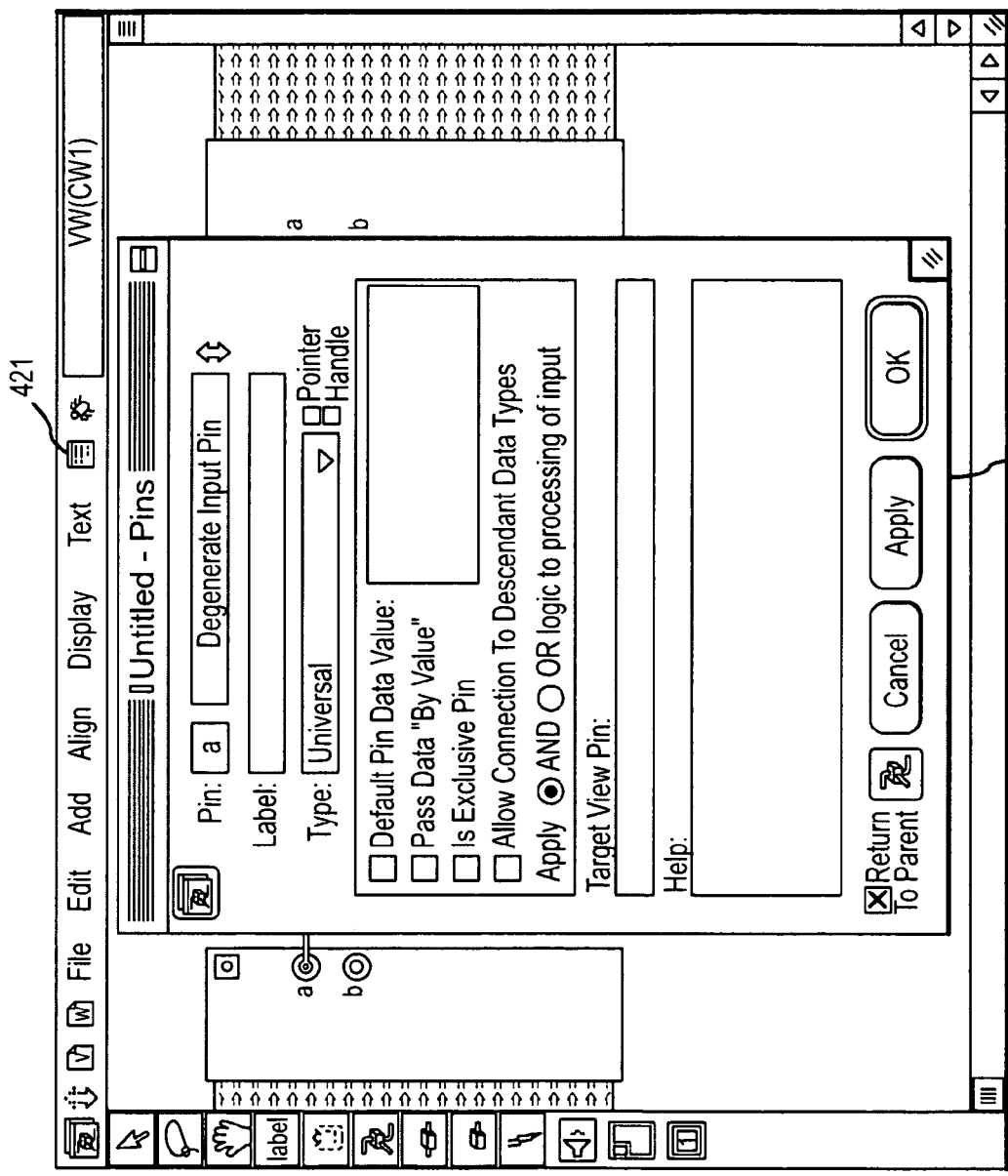
FIG. 11 illustrates a sample Pin information dialog 1100.

Referring now to FIG. 11, a sample Pin information dialog 1100 is shown. In the preferred embodiment, this dialog 1100 is generated in response to either double-clicking on a pin in the diagram or using the menu 421. Various aspects of the pin, including it's type (as preferably determined by the run-time type system) and any other logic associated with the pin and it's data-flow behavior can be set from this dialog.

Figure 12:
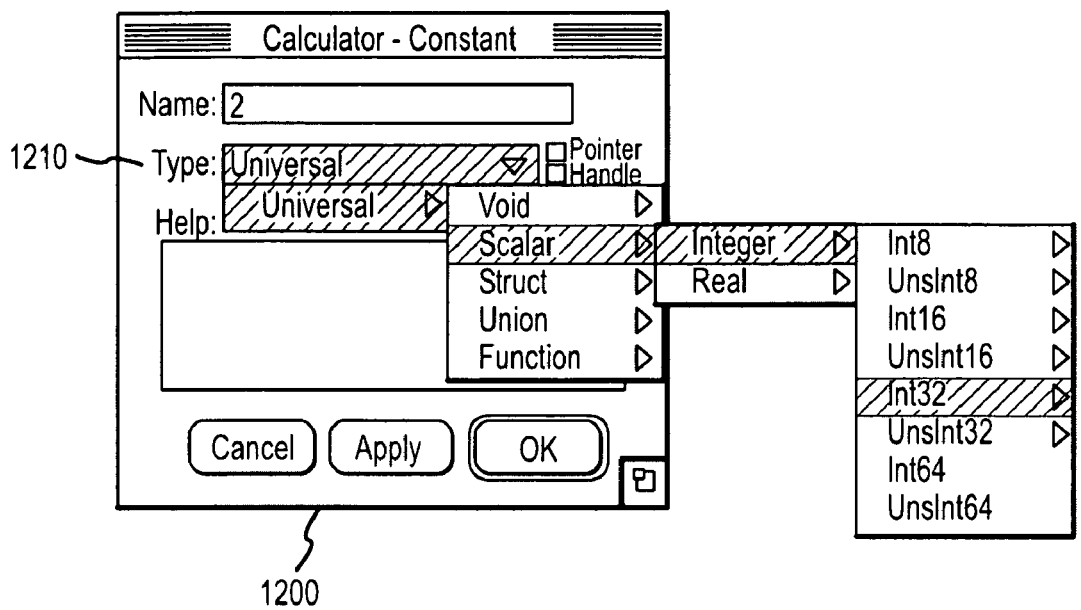
FIG. 12 illustrates a user in the process of choosing the type 1210 of a constant symbol in the WEM diagram within the type pop-up menu 1210 of the constant information window 1200.

Referring now to FIG. 12, a user in the process of choosing the type 1210 of a constant symbol in the WEM diagram within the type pop-up menu 1210 of the constant information window 1200 is shown. This further illustrates the connection between the types system provided by the substrate and the types of data on flows and pins.

Figure 13:
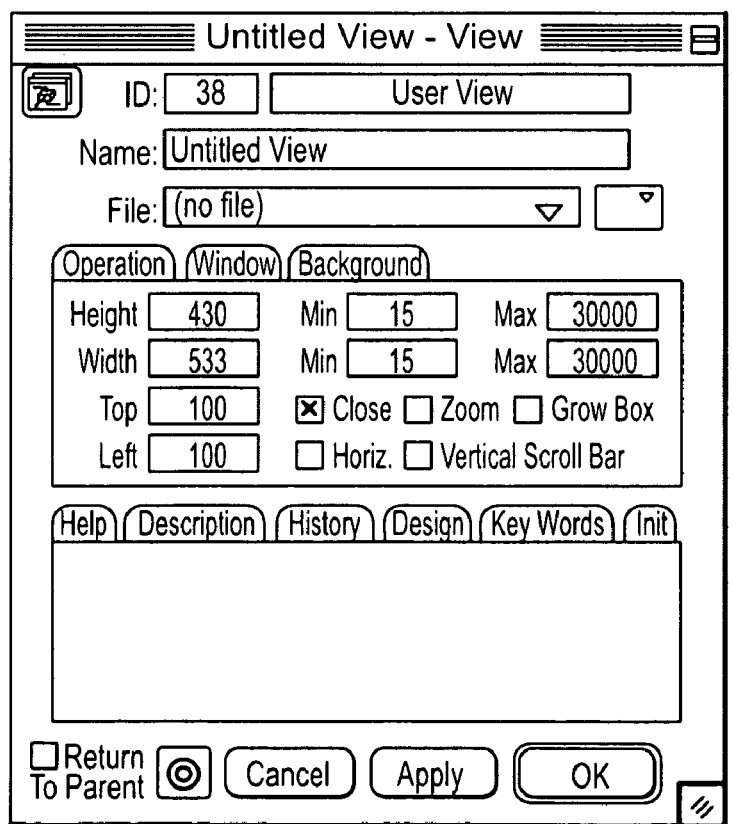
FIG. 13 illustrates a dialog window 1300 generated in connection with selection of the view or widget information window in the setup menu 421.

Referring now to FIG. 13, a dialog window 1300 generated in connection with selection of the view or widget information window in the setup menu 421 is shown. As can be seen, the dialog window 1300 allows adjustment of a wide variety of different aspects that apply to the view or widget including file path, security settings, operation behavior, visual dimensions, behaviors, and limits, and a variety of configuration and documentation descriptors.

It is clear, then, that the illustrated WEM and visual language described above allow users of the system to express and specify analytical processes in terms of data flowing between a set of computational blocks. The visual language of the present invention preferably provides the following basic features:

a) The ability to pass strongly, typed data through flows between a set of interconnected computation blocks (hereafter called widgets). Types are preferably run-time definable and examinable by the widgets themselves.

b) Widgets with typed input and output pins. Input pins provide the ability to specify default values if unconnected.

c) The ability to add arbitrary compiled code snippets to the collection of-available widgets, shareable between users of the system. Such compiled code widgets are referred to as 'atomic'.

d) After creating an algorithm by wiring together widgets into an enclosing or 'compound' widget using WEM, permitting the compound widget itself to be used as a building block for higher-level widgets. That is the language would preferably allow arbitrary nesting depth of compound widgets.

e) Because many widgets have associated UI, the graphical environment provides the ability to lay out the UI of various widgets appearing within the same window. In the preferred embodiment, within any atomic widget, an atomic GUI building environment is provided to allow layout of the atomic widget UI components. All such information is saved as part of the widget definition for sharing and later re-loading purposes.

f) Normal looping and conditional constructs are supported as are junctions and associated logic joining flows connected to multiple endpoints.

g) When scheduling, the existence of a data token on a flow must precipitate code execution on the connected flow-consumer widgets.

h) The language preferably supports the overt graphical specification of variables and constants that participate in the wiring.

i) Finally, in the preferred embodiment, a debugging means is provided, at run-time, to examine the contents and state of flows and the state of execution of all widgets involved.

Figure 14:
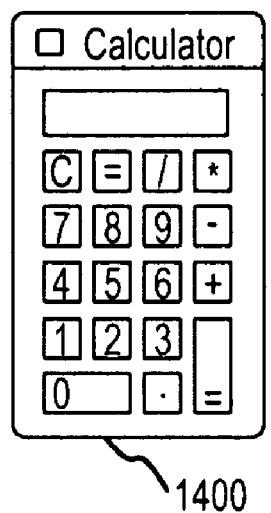
FIG. 14 illustrates a simple calculator widget/view 1400.

At the same time the data-flow wiring for a new view or widget is defined, the visual appearance is created. The interface that allows this is called View Editing Mode (VEM). Referring now to FIG. 14, a simple calculator widget/view 1400 is shown. The figure displays the structure of the view 1400 of the calculator. Each section of this figure (such as the buttons, title bar, calculator display window) can be created separately, and the individual sections of the view result in the final view, which also may be created and edited in the View Editing Mode window.

Figure 15:
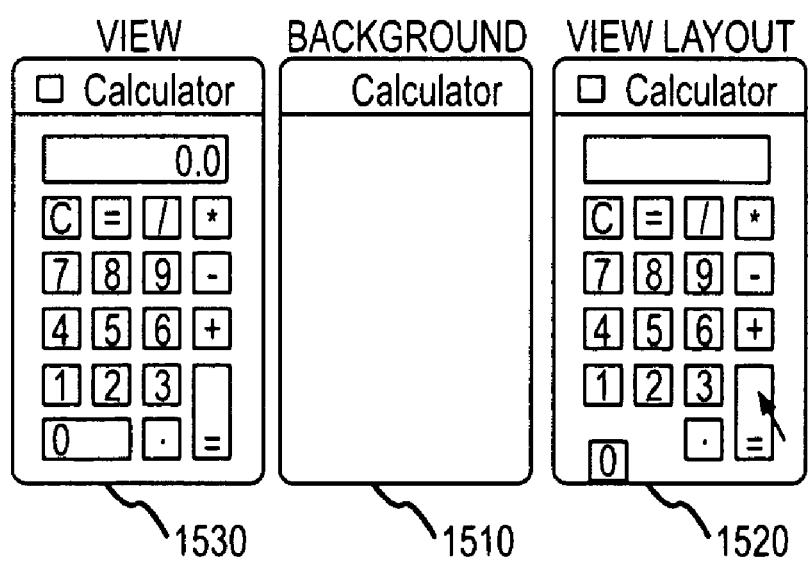
FIG. 15 illustrates the structural components of the calculator widget/view 1400.

Referring now to FIG. 15, an illustration of the structural components of the calculator widget/view 1400 is shown. In this case, the broken-down structure comprises:

Background 1510—The plain background of the calculator where the number keypad will be added;

View Layout 1520—The view layout (the keypad itself);

View 1530—The final view, including the background 1510 and view layout 1520, complete with 0.0 shown as the initial output on the display is shown.

Logically, something would need to be attached to the keys on the keypad to allow for performing calculations. Clicking the visually displayed numbers of the photograph of a calculator does not perform a function. These numbers would need to be attached to something that could actually read and manipulate them. In other words, a mere picture does nothing. Hence, once the drawing is done, the keys must be connected to an electronic device representing each individual key and its underlying meaning. This electronic equivalent, in our case, is known as a widget. Widgets are connected to the keys and act as valves that regulate the flow of electronic information. On the calculator, for instance, the widget for the 9 key would act as a valve for the constant valve 9; the plus sign (+) widget would act as the valve for the add operation. In the preferred embodiment, the VEM process allows the appearance of the calculator to be created. Once the physical appearance is complete, the internal connections must be made to enable arithmetic functions. Widgets, electronically connected to the numeric keypad of our calculator, display a different diagram, but are identical in performance to the calculator.

Figure 16:
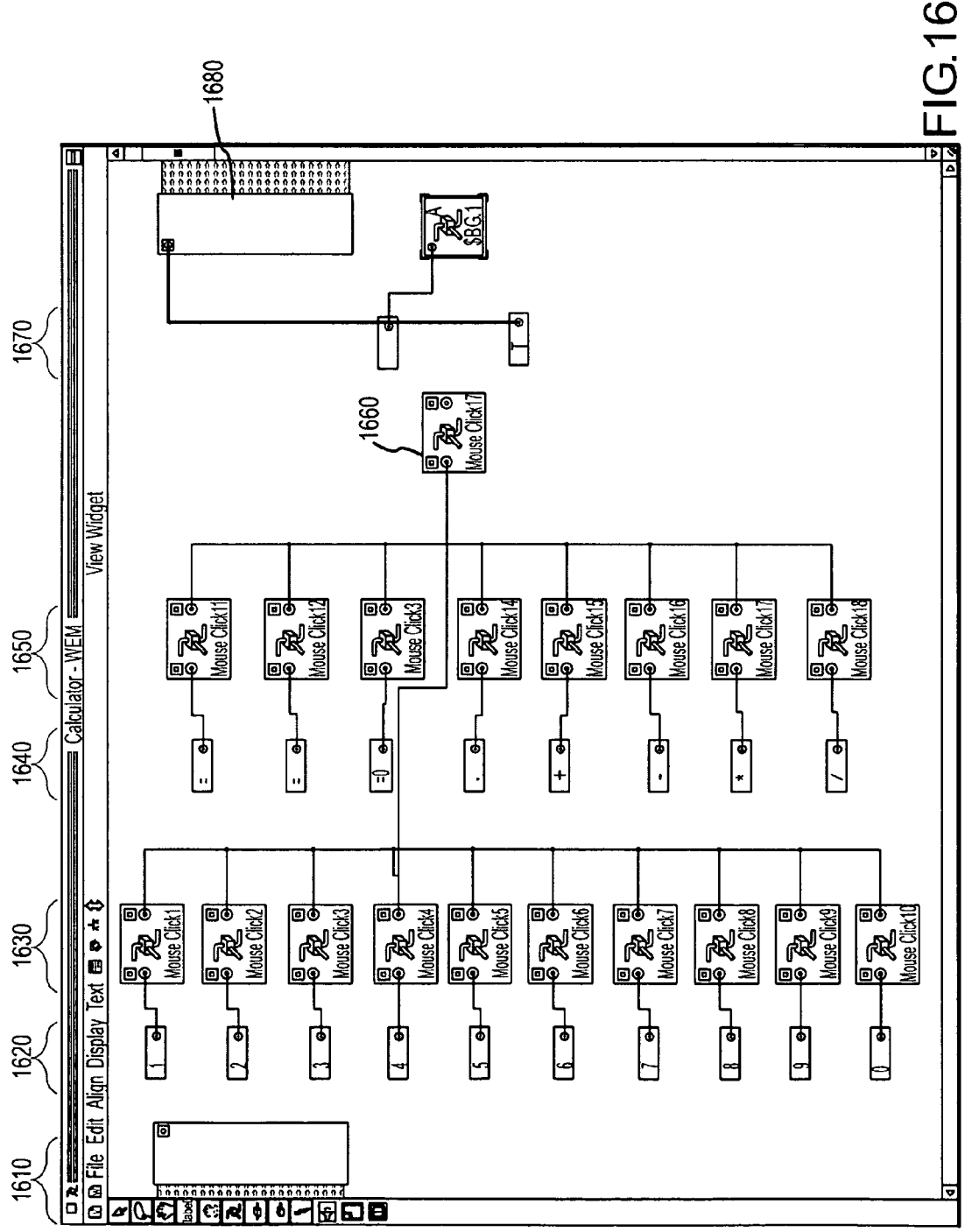
FIG. 16 illustrates an internal diagram of the calculator as it would appear in the preferred Widget Editing Mode window.

Referring now to FIG. 16, an internal diagram of the calculator as it would appear in the preferred Widget Editing Mode window is shown. This figure illustrates a view known as a view widget, which contains a collection of atomic or compound widgets, each of which may have at most one user interface region, or pane. It is in this window that users can make modifications using the WEM capabilities described above.

For explanation purposes, each individual column in the diagram is described and numbered as a single item. It is described in this fashion because each element within the column performs the same general function.

- Column 1610 displays the input bar which has no connections in this case.
- Column 1620 consists of numbered rectangles that represent the constants 0 to 9 displayed on the calculator.
- Column 1630 consists of widgets that perform like valves, regulating the data flow or the flow of the constants 1620.
- Column 1640 displays rectangles with visual operands such as the plus sign (+), the equal sign (=).
- Column 1650 contains the widgets that perform like valves, regulating the flow of the constants.
- The widget 1660 performs the sum.
- Column 1670 includes the widgets that carry the sum to the total.
- and that total is then sent to the output bar 1680.

The data-flow scheduling algorithm is the next important part of the system. The data-flow scheduling algorithm is described below by listing the algorithms for a series of recursively invoked functions. The global value "EG" is a complex structure containing various context and state information used by the environment and including the values utilized by the scheduling process.

The top level of the data-flow based scheduling algorithm is the routine SC_Scheduler( ) which is called in a continuous loop from the main thread of the environment. This routine arbitrates the scheduling of the various active views currently loaded into the environment. The principal task performed by this routine is to enforce the levels of scheduling priorities associated with the active views. To do this SC_Scheduler( ) makes use of a global active views scheduling structure which contains a set of list headers each of which points to the first element in a singularly linked list of active views having the same priority level. Because this routine locks the view being scheduled, any code operating in the main application thread that is called via this routine can be sure that pointers to structures within the current view will not become invalid during procedure execution. Code running in other threads must either lock the view, or save/restore pointers in a relative form to ensure correct pointer values across scheduling boundaries or heap movements. SC_Scheduler( ) (and everything it calls) assumes that the application thread is in a critical section (i.e., can't be preemptively disturbed). While there are outstanding events to be processed in any view, this routine alternates between scheduling the view at the top of the pending events list (and then rotating the list) and scheduling a view according to the normal view priority scheme. In this manner the system ensures that events are processed as rapidly as possible without allowing event intensive views to suppress all other scheduling. The same mechanism is repeated in SC_ScheduleView( ) to the normal tree walking algorithm.

```
void SC_Scheduler          (              // data-flow scheduler
                void
                           )              // R:void
{
    bump the scheduler cycle count
    handle any pent-up interrupt level stuff after any slot
    j = rand ( );                         // breaks certain deadly cycles!
    j = j | (1 < < (kLowestEpriority+1) ) ;   // set backstop bit
    EG->Priority = find the first bit set in cycle count word j
    if ( EG->Priority > kLowestEPriority )
    {                                     // run any background tasks
        do whatever regular monitoring etc. environment wants to do
        return;                           // at lowest priority possible.
    }
    tmp = NULL;
    pnd = NULL;
    if ( ! (EG->MitopiaFlags & kVeventBasedSlot) && EG->PendEvtHdr )
    {                                     // do views with events first
        pnd = tmp = EG->PendEvtHdr;
        EG->Priority = (*tmp)->dPriority; // set priority to match view
        EG->MitopiaFlags | =              // remember we did an event slot
            kVeventBasedSlot;
    } else                                // alternate between event and pass
    {                                     // normal slots on each
        EG->MitopiaFlags &= -             // just a plain kind of slot
            kVeventBasedSlot;
        tmp = EG->ActiveViews [EG->       // front active view at priority
            Priority] [0] ;
        pnd = 0;
    }
    SC_SetCurrentWidget(tmp,view widget   // set the chosen view widget
        (*tmp) );
    lock down the view (tmp) while we cruise around it and schedule below
    tmp = SC_ScheduleView(tmp,...) ;      // schedule a single view
    unlock the view (tmp) till the next time...
    rotate EG->ActiveView [EG->Priority] [0] to tail of list at priority
    if ( (EG->MitopiaFlags & kVeventBasedSlot) && EG->PendEvtHdr == pnd && pnd)
    {                                     // rotate pending list also
        move pnd to tail of EG->PendEvtHdr // avoids greedy event list problems
    }
}
```

As can be seen from the algorithm above, scheduling within any given view is handled entirely by the routine SC_ScheduleView( ) once the view itself has been selected based on pending event lists and priority. This routine is called by SC_Scheduler( ) to give a scheduling slot to a particular view. In most cases this amounts simply to a call to SC_ScheduleNode( ) for the view widget, but in addition this routine must deal with the special rules associated with starting and stopping views and the propagation of their tokens. Note that an exception to the fair handling of scheduling slots is made for any widgets that are waiting for non-timer related events which have occurred, these are scheduled immediately in order to ensure that events get eaten ASAP. An example of the logic that could be used to perform this routine is provided in Appendix A.

The two main routines that are called by SC_ScheduleView( ) above are SC_ScheduleNode( ) and SC_ScheduleANode( ). SC_ScheduleNode( ) is the primary function that is responsible for enforcing the rules of data-flow in the system. This routine is recursive and is responsible for implementing the depth first tree walking scheduler algorithm. In order to facilitate navigation around the various levels of the compound widgets that make up the hierarchy associated with a given view, SC_ScheduleNode( ) makes use of three basic structures: the widget descriptor record (type ET_Widget), the flow descriptor record (type ET_Flow), and the pin descriptor record (type ET_Pin). The following are the scheduler uses of the relevant fields in an ET_Widget record:

tokenHdr—This field contains the header into a dynamic list of active tokens associated with data or control flows inside a compound widget. tokenHdr=0 if the list is empty.

tokenTail—This field contains the tail (last element) of the tokenHdr list.

flowHdr—This field is the header into a static list of control and data flows inside a compound widget. FlowHdr=0 if the list is empty.

sWidgHdr—This field is the header into a list of widgets within the current compound widget. sWidgHdr=0 if the list is empty.

sWidgNext—This field contains the link elements for the list header by sWidgHdr for the surrounding compound widget (i.e., it points to the next widget in the enclosing widgets sWidgHdr list). sWidgNext=0 if no more elements in the list. The field sWidgPrev is the same but points in the reverse direction to sWidgNext.

flags—This field contains various logical flags indicating to the scheduler the state of the current widget. Of particular relevance is 'hasChildTokens' which indicates that at least one widget in the sWidgHdr list has active tokens associated with it. The flag 'hasTokens' indicates that the current widget itself has a non-empty tokenHdr list.

The following are the scheduler uses of the relevant fields in an ET_Flow record:

tokenLink—This field is the link to the next element in the tokenHdr list of the enclosing compound widget. tokenLink=0 if there are no more elements in the list.

flowLink—This field is the link to the next element in the flowHdr list of the enclosing compound widget. flowLink=0 if there are no more elements in the list.

value—This field contains a handle to the heap storage allocation for the actual data value associated with the flow (if allocated). In the case of a control flow, value=0 and the flow state is stored in one of the Flags field bits.

cIpinHdr—This field contains the header into a static list of contained widget input pins that are connected to the current flow. cIpinHdr=0 if the list is empty. Note that an input pin to compound widget may be in the connected input pin list for a flow within the widget that contains it's parent while also being in the connected output pin list of a flow internal to its parent.

cOpinHdr—This field contains the header into a static list of contained widget output pins that are connected to the current flow. cOpinHdr=0 if the list is empty. Note that an output pin of compound widget may be in the connected output pin list for a flow internal to its parent, while also being in the connected input pin list of a flow within the widget that contains it's parent.

flags—This field contains various logical flags indicating to the scheduler the state of the flow. 'isControlflow' indicates that the flow is a control rather than a data flow. 'hasToken' indicates that the flow has a token associated with it. 'useORlogic' specifies OR rather than AND consumption logic. 'unConsumable' indicates that tokens associated with the flow cannot be consumed. 'hasBreakPoint' and 'hasWatchPoint' are used to initiate debugging activities.

The following are the scheduler uses of the relevant fields in an ET_Pin record:

cIpinLink—This field is the link to the next element in the cIpinHdr list of the connected flow. cIpinLink=0 if no more elements in the list.

cOpinLink—This field is the link to the next element in the cOpinHdr list of the connected flow. cOpinLink=0 if no more elements in the list.

parent—This field contains a reference to the widget record for the widget whose input/output pin this ET_Pin record describes.

During normal processing, the scheduler algorithm attempts to walk any given tree (view) in the environment's active views list and when it finds an active token that can potentially be consumed by running or resuming an atomic widget, it does so. The algorithm is predicated on the following facts:

The mission of the scheduling algorithm is to attempt to consume any active data flow tokens in the view, thereby completing the view.

Only atomic widgets actually do anything, so the algorithm must continue to walk the tree until it finds an atomic widget whose input is connected to an active data flow, and then execute it (if possible) in the hope that the widget will complete thereby consuming all outstanding tokens connected to its inputs.

Many widgets produce more tokens on their outputs after consumption of the input tokens.

Because a widget (atomic or compound) only consumes tokens on its inputs when it completes, this means that all ancestral (i.e., enclosing) compound widgets of any atomic widget that has not yet completed, must also have unconsumed tokens on their inputs. This in turn means that the scheduler is guaranteed to find all outstanding tokens in a view, no matter how deeply they are nested, simply by looking at only those enclosing widgets. For each level in the tree that has outstanding tokens, the enclosing widgets will have outstanding tokens on their inputs as well. The result is that rather than having to examine every compound widget in a WEM diagram tree, or even every data flow in the WEM tree, the scheduler can be sure that by examining only what is connected to data flows with active tokens, it has examined every widget in the view that has the potential to execute. Within any given compound widget, this list is referred to as the token list. These lists are preferably arranged in a tree structure that can be traced all the way back to the view widget itself. At any given moment, there are vastly fewer active tokens within a view than there are either widgets or data flows. Hence, the efficiency of this algorithm greatly exceeds other tree traversal strategies.

Whenever an atomic widget consumes its input tokens, it does so by removing them from the token list of the enclosing compound widget. If this token list becomes empty then the compound widget itself has completed and the scheduler should therefore consume any tokens on it's inputs and generate the necessary output tokens in the parent WEM of the compound widget. This process continues all the way up the tree until the scheduler detects an empty tree at which time the view is complete.

The scheduler tree traversal algorithm is recursive, i.e., it calls itself repeatedly as it walks down the tree, starting at the view widget until it finds a leaf node (atomic widget) that can be scheduled. It then either starts or resumes that widget and when the widget completes, it returns back up the calling chain. As the algorithm climbs back up the path it rotates the token list for every level in the tree by moving the token that was at the front of the list (i.e., the one that determined which attached widget it chose in the downward path), to the back. The effect of this repeated descent and ascent algorithm is to allocate sequential time slices, at any given level of the tree, to widgets that are as far apart as possible in the tree. This is designed to prevent undesirable bunching of time allocations to a given compound widget. Atomic widgets that are higher up in the tree will get more time slices than those that are further down. This is as it should be since higher up atomic widgets generally correspond to UI related displays and controls which must be as responsive as possible, and which will not actually be eligible to run unless the UI event on which they are waiting has occurred. One possible side effect of the algorithm is that at any given level, the smaller branches of an unbalanced tree get more scheduling slots than larger ones. A tree-balancing algorithm, if desired, could correct this behavior. This algorithm returns to the caller (SC_Scheduler) after a single descent and ascent. SC_Scheduler( ) itself then selects another view and priority group and repeats the process. Thus available CPU time slots are distributed over all views in the system according to priority. Widgets in many other views may be scheduled before SC_Scheduler( ) again returns to this view and performs another descent and ascent of this tree. Sample code for one embodiment of SC_ScheduleNode is provided in Appendix A.

The logic for SC_ScheduleANode (schedule atomic node) is broken out separately from SC_ScheduleNode( ) so that nodes that are atomic can be forcefully scheduled based on non-data-flow related events. Sample code for SC_ScheduleANode( ) is provided in Appendix A.

The routine SC_StartWidget( ) is responsible for checking that all the necessary conditions have been met for starting a particular widget. This routine is therefore responsible for enforcing the rules of data flow as well as the modifications to these rules described above. Once SC_StartWidget( ) has determined that a widget is eligible to run, it actually launches it using either SC_StartAWidget( ) or SC_StartC-widget( ) (depending on whether the widget is atomic or compound). If the widget concerned is ineligible to run for any reason, this routine returns FALSE otherwise it returns TRUE. This routine can also be called with the parameter 'JustCheckin' set to TRUE in which case it makes all necessary checks for eligibility (other than those for input availability) but does not actually cause the widget to be started. That is, it calls itself under certain circumstances in order to find out if widgets that are descendant from the current widgets (in terms of data flow, not hierarchy) have started or are ready to start. Sample code for this Algorithm is provided in Appendix A. This routine is recursive.

The function SC_StartAwidget( ) is called by SC_StartWidget( ) once it determines that all the necessary conditions have been met to actually initiate execution of an atomic widget. Initiating execution of an atomic widget involves creating a seperate execution thread for that widget to run in. In order to maintain this seperate thread, the thread manager software requires a seperate stack area which the atomic widget will use once launched. Every atomic widget contains a stackSize field which gives the maximum size of stack that the widget anticipates will be required in order to execute. Because the atomic widget retains control of the CPU once the thread has been launched, the scheduler has no way of preventing erroneous widgets from stepping outside their stated stack allocation and thus corrupting the heap. It is therefore very important that widgets ensure that this does not occur. This routine can however detect that such an error has occured after the fact and when widget execution completes, SC_StartAwidget( ) will report an appropriate error if stack debugging is enabled. The mechanism used is to place test patterns at various points within the allocated stack area, especially at the end point. When widget execution completes, these patterns will have been erased up to the deepest point that the widgets stack reached. If the test pattern at the end of the allocation has been overwritten then the widget is erroneous, otherwise the other test patterns may be used to determine actual stack requirements. Filling an area of heap with these test patterns consumes time and stack debugging should preferably be enabled only when developing new atomic widgets. Because a widgets initialization code may contain suspends, this routine may be re-entered a number of times for the same widget before initialization is complete. By returning a false for inclomplete initialization and not setting the "kIsRunning" flag, we can be sure that SC_ScheduleNode( ) will keep calling us until done. Sample code for one embodiment of SC_StartAWidget is provided below:

```
Boolean SC__StartAwidget      (                              // Start atomic widget
execution
                    ET__ViewHdl       aView,                 // I:View handle
                    ET__WidgetPtr     aWidP,                 // I:widget record
pointer
                    Boolean           InitializeOnly         // I:if TRUE, just
initialization
                                      )                      // R:TRUE if started
{
    if ( aWidP->wThreadID )                                  // thread was already
running
    {
        if ( !(FLAGS(aWidp) & kHasBeenInitialized) )         // resume/start
initialize
            SC__ResumeWidget (aView,aWidP,NO);               // Resume the widget
    }
    if ( !((FLAGS(aWidP) & kHasgeenInitialized) | | aWidP->wThreadID) )
    {                                                        // make a widget thread
        aWidp->wThreadID = create new thread
            err = yield to thread(aView,&aWidp,kInitializeEntryPt...);
```

```
                        }
        if ( !InitializeOnly && !(FLAGS(*aView) & kKillThisView) )
        {
            if ( !err && (FLAGS(aWidP) & kHasBeenInitialized) )
                err = yield to thread (aview,&aWidp,kExecuteEntryPt...);
        }
        return (err == 0 && (FLAGS(aWidP) & kHasBeenInitialized) );
    }
```

The routine SC_StartCwidget( ) starts execution of a compound widget once all the necessary preconditions have been satisfied. Since there is no code associated with a compound widget, the process of starting one essentially consists of copying the tokens on the external input pins into the internal flows of the compound widget so that these may in turn stimulate contained widgets into execution. Sample code for one embodiment of SC_StartCWidget is provided below:

In the preferred embodiment, the routine SC_ResumeWidget( ) resumes execution of an atomic widget that has previously suspended by calling SC_Suspend( ) either directly or indirectly. This function assumes that all necessary conditions for execution have been checked at the time the widget was started and thus it does not need to repeat such checks. Resumption of an executing widget essentially consists of an explicit yield to the relevant thread. The only subtelty in SC_ResumeWidget( ) is its use to generate

```
Boolean SC_StartCwidget       (                        // Start compound widget execution
                    ET_ViewHdl      aView,             // I:View handle
                    ET_WidgetPtr    aWidP              // I:widget record pointer
                    )                                  // R:TRUE if widget was started
{
    oldFlags = FLAGS(aWidP);
    FLAGS(aWidp) |= kIsRunning + kHasBeenInitialized;   // set widget's init & run flags
    for (all formal and degenerate inputs)
    {
        mask = get the masks for available inputs
        i = get count of number of pins of that type
        while ( i )                                    // for all pins of this type
        {
            i--;
            pinName = i + 'A' or 'a';
            pin = get the pin concerned
            iflow = get the flow connected to it within the compound widg.
            xflow = get the flow connected to it outside the compound widg.
            if ( iflow )
            {
                SC_AddAToken(iflow);                   // add a token to internal flow
                if ( iflow->value )                    // dispose of old data (if any)
                    TM_DisposeHandle (0, (anonHdl) iflow->value,...);
                if ( !xflow )                          // if pin input ! available
                {                                      // pin must have been defaulted
                    iflow->value = pin->pDefault;
                } else iflow->value = xflow->value;    // external to internal copy
            }
        }
    }
    if ( ret ) SC_SpontaneousTokens (aWidP);           // generate spontaneous tokens
    if ( aWidP == view widget(*EG->CurrentView) && ! (oldFlags & kHasBeenInitialized)
    {                                                  // routine to init. everything
        SC_InitializeCompoundAtomics (EQ->CurrentView,aWidP);
    }
    return ret;
}
``` certain time based events (idle, tick, second) prior to resuming the thread if the specified time interval has elapsed and the widget is waiting for the time based event specified.

In the preferred embodiment, the routines SC_CheckCtrlStop( ) and SC_CheckCtrlStart( ) may be used to check a flow connected to a control pin to determine if it implies that a widget should be stopped/started. In the preferred embodiment, the routine SC_TimeToGobbleInputs( ) may be used by the scheduler to determine if it should schedule a given widget based on the state of it's input pins. The logic is complicated by the fact that 'exclusive' pins can cause widgets to fire even when only a subset of the inputs is available.

In the preferred embodiment, the routine SC_Trace2Inputs( ) can be used to check all the outputs of a given widget 'aWidP' to see if they directly or indirectly lead to completing the required inputs of a second widget 'cwidg'. The purpose of this is to implement the 'as needed' function whereby widgets that are marked as 'as needed' will only be scheduled by the environment when by running, their outputs might potentially cause another normal widget to become eligible to run. This is the behavior required of many UI type widgets such as dialogs. See SC_StartWidget( ) for usage.

In the preferred embodiment, the routine SC_StopCWidget( ) is called to complete execution of a compound widget. As for atomic widgets, completing compound widget execution involves propagating tokens onto the output flows. Since the output flows of the compound widget may be busy, there is a possibility that the token propagation routine (SC_PropagateTokens( )) may hang up. To simplify this problem, a seperate temporary thread is created to perform the compound widget completion action thus allowing for the possibility of backup. Unlike conventional widget threads referenced from the wThreadID field of the widget record, the threads associated with completing compound widgets are torn down and re-cycled as soon as the token propagation is complete, also these threads only execute internal environment code, not widget code. Note that because the thread may back up, it may be resumed in SC_ScheduleNode( ) many times before completing.

In the preferred embodiment, the routine SC_SpontaneousTokens( ) is called whenever a compound widget is started by the scheduler, and is responsible for generating any spontaneously produced tokens contained within the WEM diagram for that widget. Spontaneously produced tokens are generally associated with constant symbols. Note that although flows with variable symbols attached have unconsumable tokens on them, these tokens are not generated until the flow is first written to, i.e., they are not spontaneous. This routine does not check for whether the output flow is busy and hang up waiting for it to be clear. This is because this is not possible given the fact that this routine is called during widget starting at which time all internal flows are by definition free. Anyway to do so would be fatal to the main thread. In the preferred embodiment, the routine SC_AddAToken( ) adds a token to an existing flow.

In the preferred embodiment, the routine SC_InitializeCompoundAtomics( ) is recursive and initializes all atomic widgets within the specified compound widget and any compound widgets it contains either by calling SC_StartAWidget( ) or by recursively calling itself as required.

Widget Pin Access API

The API definition below gives the basic public calls available to widgets/threads when accessing data on input pins and writing data to output pins. The API is intended to be illustrative only and is by no means complete. The header files for a sample API implementation is provided in Appendix B.

In the preferred embodiment, the function PC_NumDataInputs( ) examines the Widget Input List contained in the specified (or defaulted) widget and returns the counts of the number of formal and degenerate input pins. In the preferred embodiment, the function PC_NumDataOutputs( ) examines the Widget Output List contained in the specified (or defaulted) widget and returns the counts of the number formal and degenerate output pins.

In the preferred embodiment, the function PC_GetDataInput( ) takes an input specifier ('A'<=char<='Z' or 'a'<=char<='z') and returns a handle to the storage value for that input or NULL if not found, or if the value of the connected flow is invalid. The handle returned by PC_GetDataInput( ) would preferably NEVER be de-allocated by widget code. The handle returned may be subject to relocation or resizing by the scheduler across any scheduling boundary.

In the preferred embodiment, the function PC_GetDataInputType( ) takes an input specifier ('A'<=char<='Z' or 'a'<=char<='z') and returns the type ID for that type. In the preferred embodiment, the function returns zero if the input was not found. The widget may use the returned type ID to obtain further information about the type using the routines provided by the type manager package. In the preferred embodiment, the function PC_GetDataOutputType( ) performs a similar function for output pins. In the preferred embodiment, the function PC_SetDataInputType( ) takes an input specifier ('A'<=char<='Z' or 'a'<=char<='z') and a type ID, and sets the type field of the corresponding pin to match the type ID. PC_SetDataOutputType( ) may be used to do the same for output pins.

In the preferred embodiment, the function PC_GetDataInputName( ) takes an input specifier ('A'<=char<='Z' or 'a'<=char<='z') and returns a handle to the name string for that input or NULL if not found or unnamed. The caller should dispose of the handle returned by this routine when the string is no longer required. In the preferred embodiment, the function PC_GetDataOutputName( ) is used for output pins.

In-the preferred embodiment, the function PC_IsDataInputConnected( ) takes an input specifier ('A'<=char<='Z' or 'a'<=char<='z') and returns a Boolean indicating whether the input is connected or not. If the input does not exist, a FALSE is returned. Note that if the input is degenerate and PC_IsDataInputConnected( ) returns FALSE, the input may still have a default value assigned to it which can be retrieved using PC_GetDataInput( ). Thus the combination of a FALSE from PC_IsDataInputConnected( ) with a non-NULL result from PC_GetDataInput( ) uniquely defines a defaulted degenerate input. A TRUE from PC_IsDataInputConnected( ) together with a null result from PC_GetDataInput( ) indicates an invalid data flow connected to the input. This routine is provided in order to allow atomic widgets to implement the logic associated with degenerate input pins. Because formal inputs are by definition connected (enforced by WEM), this routine simply returns TRUE when called for formal inputs.

In the preferred embodiment, the function PC_IsDataOutputConnected( ) takes an output specifier ('A'<=char<='Z' or 'a'<=char<='z') and returns a Boolean indicating whether the output is connected or not. If the output does not exist, a FALSE is returned. This routine is provided in order to allow atomic widgets to implement the logic associated with degenerate output pins. Because formal outputs are by definition connected (enforced by WEM), this routine simply returns TRUE when called for formal outputs. In the preferred embodiment, the function PC_DoesOutputHaveToken( ) can be used to determine if a particular output exists for a widget and has an unconsumed token value already assigned, TRUE is returned in this case, otherwise FALSE.

In the preferred embodiment, the function PC_SetDataOutput( ) takes an output specifier ('A'<=char<='Z' or 'a'<=char<='z') and assigns a new value to it. The function preferably returns a Boolean indicating whether the assignment was completed successfully or not. The value is passed to PC_SetDataOutput( ) as a void pointer reference, together with an integer parameter specifying the size of the output object to be created. This routine copies the value into the output value handle in the heap, creating or resizing the handle as necessary. If the output flow already has a token associated with it, this function creates a temporary storage allocation to hold the value. The scheduler will copy any temporary storage values into the connected output data flow when widget execution is complete and the connected output flow becomes free to accept new tokens. Once the value has been copied, the original passed in via the 'data' parameter may be discarded. The only output of this function is the updated value in the heap and flag settings in the widget record.

In the preferred embodiment, the function PC_SetControlOutput( ) sets the value of the control output pin to either true or false. Most normal atomic widgets will not need to use this function since the environment will by default set the control output to false when the widget begins execution and true on completion. Only those widgets that are performing loops or synchronizing functions and whose control output is intended for modifying the normal scheduling sequence of the WEM diagram within which the widget resides will explicitly control this pin using PC_SetControlOutput( ). The effect of these values on the external WEM are:

TRUE—This will cause any externally connected widget to be eligible to run

FALSE—Any externally connected widget will be ineligible to run

Note that because control flow values change in the external WEM diagram immediately they are written (as opposed to data flows which change when the writing widget terminates), this routine must also perform the necessary logic to maintain the environment flow and token lists as a result of any value change. For data flows, the Scheduler performs this logic when an atomic widget completes.

In the preferred embodiment, the function PC_GetInputFlowName( ) takes an input specifier ('A'<=char<='Z' or 'a'<=char<='z') and returns a handle to the name of the flow in the surrounding WEM diagram that is connected to that input or NULL if not found. The caller should dispose of the handle returned by this routine when the string is no longer required. In the preferred embodiment, the function PC_GetInputFlowType( ) takes an input specifier ('A'<=char<='Z' or 'a'<char<='z') and returns the type ID for the flow connected to that pin. In the preferred embodiment, the function returns zero if the input was not found. The widget may use the returned type ID to obtain further information about the type using the routines provided by the type manager package. Note that the type of the flow and the type of the input pin are normally the same and hence a call to PC_GetDataInputType( ) would suffice, however certain widgets that accept a given parent type (e.g., scalar) may wish to examine the type of the flow actually connected in order to determine which descendant type was actually connected (e.g., double, int32 etc.).

In the preferred embodiment, the function PC_GetOutputFlowName( ) takes an output specifier ('A'<=char<='Z' or 'a'<=char<='z') and returns a handle to the name of the flow in the surrounding WEM diagram that is connected to that output or NULL if not found. The caller should dispose of the handle returned by this routine when the string is no longer required. In the preferred embodiment, the function PC_GetOutputFlowType( ) takes an output specifier ('A'<=char<='Z' or 'a'<=char<='z') and returns the type ID for the flow connected to that pin. In the preferred embodiment, the function returns zero if the output was not found. The widget may use the returned type ID to obtain further information about the type using the routines provided by the type manager package. Note that the type of the flow and the type of the output pin are normally the same and hence a call to PC_GetOutputType( ) would suffice.

In the preferred embodiment, the function PC_DoesInputExist( ) can be used to determine if a particular input exists for a widget, TRUE is returned if the input exists, otherwise FALSE. In the preferred embodiment, the function PC_DoesOutputExist( ) is similar for outputs.

In the preferred embodiment, the function PC_GetStaticDataInput( ) takes an input specifier ('A'<=char<='Z' or 'a'<=char<='z') and returns a handle to the storage value for that input or NULL if not found. Unlike the routine PC_GetDataInput( ), this routine will also search on flows that have no associated token for an attached constant object or defaulted output and return any value found. This means that this routine will operate at initialize time as well as execute time. This routine also has the ability to monitor changes on an input flow at run time that do not necessarily have a token associated with them. This often occurs when a widget has written a value onto a flow but has not yet completed and thus has posted no tokens. Use of this "tokenless" communication path is strongly discouraged except in exceptional circumstances. The handle returned by PC_GetDataInput( ) should NEVER be deallocated by widget code. The handle returned may be subject to relocation or resizing by the scheduler across any scheduling boundary, widgets should be careful not to de-reference the handle and use the de-reference value across such a boundary. Widgets should avoid "Locking" data handles where possible since this will reduce the schedulers ability to resize the handle in response to new data.

The foregoing description of the preferred embodiments of the invention has been presented for the purposes of illustration and description. For example, although described with respect to the C programming language, any language could be used to implement this system. The descriptions of the header structures should also not be limited to the embodiments described. While the sample pseudo code provides examples of the code that may be used, the plurality of implementations that could in fact be developed is nearly limitless. For these reasons, this description is not intended to be exhaustive or to limit the invention to the precise form disclosed. Many modifications and variations are possible in light of the above teaching. It is intended that the scope of the invention be limited not by this detailed description, but rather by the claims appended hereto.

The invention claimed is:

1. A system for implementing large-scale asynchronous token based distributed data-flow based applications comprising:

a) a data-flow based scheduling environment for managing an execution of one or more control-flow based functional building blocks, or widgets, based on one or more rules of data flow enforced by said scheduling environment outside of said widgets;

b) a visual programming environment, wherein said visual programming environment provides the ability to build and control a flow of data collections between said one or more widgets within said scheduling environment;

c) a pin-based application programming interface that provides access to contents from an executing code within said one or more widgets through one or more widget input pins; and d) a strongly-typed run-time discoverable types system for defining types of said flow of data collections presented to said one or more widget input pins at run-time;

wherein execution of said one or more widgets is triggered asynchronously by said flow of data collections arriving at said one or more widget input pins causing said one or more widgets to perform one or more actions in response to said flow of data collections arriving at said one or more widget input pins.

2. The system of claim 1, wherein said data-flow based scheduling environment includes one or more scheduler routines, wherein said one or more scheduler routines help balance the needs of data initiated program execution with considerations such as user responsiveness.

3. The system of claim 1, wherein said data-flow based scheduling environment includes one or more scheduler routines, wherein said one or more scheduler routines help balance the needs of data initiated program execution with considerations such as a hierarchy of said one or more widgets.

4. The system of claim 1, wherein said one or more widgets are network distributed.

5. The system of claim 1, wherein a programming language supports the creation of a layout and specification of a visual appearance of said one or more widgets that are running in a user interface.

6. The system of claim 1, wherein each of said one or more widgets having said one or more widget input pins which are interconnected via typed flows which transfer data from an output pin of a source to an input pin of a sink in a tokenized manner, wherein data is consumed in said execution of said one or more widgets.

7. The system of claim 1, wherein said visual programming environment can be used to develop one or more atomic widgets, said one or more atomic widgets containing a compiled executable code.

8. The system of claim 7, wherein said visual programming environment can be used to develop one or more compound widgets, said one or more compound widgets including an inner structure that defines any subordinate widgets that are required to implement a functionality of said one or more compound widgets.

9. The system of claim 8, wherein said one or more atomic widgets are embedded into said one or more compound widgets.

10. The system of claim 9, wherein said visual programming environment can be used to develop said one or more widgets that are instantiated within one or more container objects, or views, which associate a user interface to said one or more widgets.

11. The system of claim 10, wherein said visual programming environment can be used to assign one or more priorities to a view level and said one or more priorities can be used by said scheduling environment.

12. The system of claim 8, wherein each of said one or more compound widgets includes one or more constants and one or more variables within a data-flow definition.

13. The system of claim 8, wherein said one or more compound widgets includes a specification of the types of values associated with any flow, pin, constant, or variable based on types defined within said strongly-typed run-time discoverable types system.

14. The system of claim 8, further comprising a graphical run-time debugging environment that permits examination and alteration of a state of all typed data internal to any said one or more compound widgets or any said one or more widget input pins.

15. The system of claim 1, wherein each of said one or more widgets includes a control input pin that determines whether said one or more widgets will run.

16. The system of claim 15, wherein each of said one or more widgets includes a control output pin.

17. The system of claim 15, wherein any control flow connections between said one or more widgets are level-based and cannot be consumed.

18. The system of claim 1, wherein each of said one or more widgets includes a formal input and a formal output.

19. The system of claim 1, wherein each of said one or more widgets includes at least one degenerate input and at least one degenerate output.

20. The system of claim 19, wherein said at least one degenerate input and said at least one degenerate output have default values.

21. The system of claim 1, wherein said types system is a strongly-typed distributed run-time system capable of describing and manipulating arbitrarily complex non-flat binary data derived form type descriptions in a standard programming language.

22. The system of claim 1, wherein data structures created by said visual programming environment use a memory model that creates a handle and a reference to an item in said handle, wherein said reference is created using an offset value that defines a physical offset of data within a memory block.

23. The system of claim 1, wherein said data-flow based scheduling environment supports specification of an 'OR' consumption that results in a consumption of a data token by a first widget that has inputs available for said data token.

24. The system of claim 1, wherein said data-flow based scheduling environment supports specification of an 'AND' consumption that results in a consumption of a data token only when all connected of said one or more widgets have run.

25. The system of claim 24, wherein said data-flow based scheduling environment does not permit said data token to be added to a flow until an existing data token is consumed.

26. The system of claim 1, further comprising one or more widget packs, wherein each said one or more widgets in said widget pack shares a common context but can independently execute in accordance with said scheduling environment.

27. The system of claim 1, wherein said data-flow based scheduling environment can run any of said one or more widgets to enable another of said one or more widgets to run according to said one or more rules of data flow.

28. A method for implementing large-scale asynchronous token based distributed data-flow based applications, the method comprising the steps of:

a) executing one or more control-flow based functional building blocks, or widgets, based on one or more rules of data flow enforced by a data-flow based scheduling environment outside of said widgets;
b) building and controlling, in a visual programming environment, a flow of data collections between said one or more widgets within said data-flow based scheduling environment;
c) accessing, through a pin-based application programming interface, contents from an executing code within said one or more widgets through one or more widget input pins;
d) defining types of said flow of data collections presented to said one or more widget input pins at run-time through a strongly-typed run-time discoverable types system;
e) triggering asynchronously said executing step by said flow of data collections arriving at said one or more widget input pins; and
f) performing by said one or more widgets one or more actions in response to said flow of data collections arriving at said one or more widget input pins.

* * * * *